United States Patent (10) Patent No.: US 8,884,813 B2
Bangera et al. (45) Date of Patent: Nov. 11, 2014

(54) SURVEILLANCE OF STRESS CONDITIONS OF PERSONS USING MICRO-IMPULSE RADAR

(75) Inventors: Mahalaxmi Gita Bangera, Renton, WA (US); Roderick A. Hyde, Redmond, WA (US); Muriel Y. Ishikawa, Livermore, CA (US); Edward K. Y. Jung, Bellevue, WA (US); Jordin T. Kare, Seattle, WA (US); Eric C. Leuthardt, St. Louis, MO (US); Nathan P. Myhrvold, Bellevue, WA (US); Elizabeth A. Sweeney, Seattle, WA (US); Clarence T. Tegreene, Bellevue, WA (US); David B. Tuckerman, Lafayette, CA (US); Thomas Weaver, San Mateo, CA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 368 days.

(21) Appl. No.: 12/930,254

(22) Filed: Dec. 30, 2010

(65) Prior Publication Data
US 2012/0116202 A1 May 10, 2012

Related U.S. Application Data

(63) Continuation-in-part of application No. 12/930,043, filed on Dec. 22, 2010, and a continuation-in-part of
(Continued)

(51) Int. Cl.
*G01S 13/00* (2006.01)
*G08B 23/00* (2006.01)
(Continued)

(52) U.S. Cl.
CPC ............ *A61B 5/0507* (2013.01); *G01S 13/887* (2013.01); *A61B 5/024* (2013.01); *G01S 13/52* (2013.01); *G01S 13/867* (2013.01); *A61B 5/0816* (2013.01); *G01S 7/415* (2013.01); *G01S 7/412* (2013.01); *A61B 5/165* (2013.01); *G01S 13/88* (2013.01); *A61B 5/113* (2013.01); *A61B 5/7253* (2013.01); *G01S 13/0209* (2013.01)
USPC .......... 342/90; 342/175; 342/189; 340/573.1; 340/573.4; 340/573.7

(58) Field of Classification Search
USPC ................. 342/52–58, 89–97, 175, 189, 197; 340/573.1, 573.4, 573.5, 573.7; 382/103, 115; 600/453; 352/52–58, 352/89–97, 175, 189, 197
See application file for complete search history.

(56) References Cited

U.S. PATENT DOCUMENTS 3,796,208 A * 3/1974 Bloice ........................... 600/534
4,513,748 A * 4/1985 Nowogrodzki et al. ...... 600/453
(Continued)

OTHER PUBLICATIONS

PCT International Search Report; International App. No. PCT/US2011/001790; Feb. 3, 2012; pp. 1-2.
(Continued)

*Primary Examiner* — Peter Bythrow
(74) *Attorney, Agent, or Firm* — Dorsey & Whitney LLP

(57) ABSTRACT

One or more computers are configured to determine a human stress condition corresponding to one or more physical or physiological parameters extracted from one or more micro-impulse radar (MIR) signals.

14 Claims, 9 Drawing Sheets

Related U.S. Application Data application No. 12/928,703, filed on Dec. 16, 2010, and a continuation-in-part of application No. 12/925,407, filed on Oct. 20, 2010, which is a continuation-in-part of application No. 12/924,036, filed on Sep. 17, 2010, which is a continuation-in-part of application No. 12/655,808, filed on Jan. 5, 2010.

(51) Int. Cl.
| | |
|---|---|
| *A61B 5/05* | (2006.01) |
| *G01S 13/88* | (2006.01) |
| *G01S 13/52* | (2006.01) |
| *G01S 13/86* | (2006.01) |
| *G01S 7/41* | (2006.01) |
| *A61B 5/16* | (2006.01) |
| *G01S 13/02* | (2006.01) |
| *A61B 5/024* | (2006.01) |
| *A61B 5/08* | (2006.01) |
| *A61B 5/113* | (2006.01) |
| *A61B 5/00* | (2006.01) |

(56) References Cited

U.S. PATENT DOCUMENTS

| | | | |
|---|---|---|---|
| 4,931,865 A * | 6/1990 | Scarampi | 725/12 |
| 4,958,638 A * | 9/1990 | Sharpe et al. | 600/407 |
| 5,226,425 A * | 7/1993 | Righter | 600/523 |
| 5,305,748 A * | 4/1994 | Wilk | 600/407 |
| 5,361,070 A * | 11/1994 | McEwan | 342/21 |
| 5,448,501 A * | 9/1995 | Hablov et al. | 340/573.1 |
| 5,507,291 A * | 4/1996 | Stirbl et al. | 600/407 |
| 5,519,400 A * | 5/1996 | McEwan | 342/28 |
| 5,573,012 A * | 11/1996 | McEwan | 600/595 |
| 5,766,208 A * | 6/1998 | McEwan | 600/595 |
| 5,774,091 A | 6/1998 | McEwan | |
| 5,850,470 A | 12/1998 | Kung et al. | |
| 5,905,436 A * | 5/1999 | Dwight et al. | 340/573.1 |
| 6,011,477 A * | 1/2000 | Teodorescu et al. | 340/573.1 |
| 6,062,216 A * | 5/2000 | Corn | 128/204.23 |
| 6,083,172 A * | 7/2000 | Baker, Jr. et al. | 600/500 |
| 6,122,537 A * | 9/2000 | Schmidt | 600/407 |
| 6,211,863 B1 | 4/2001 | Chery et al. | |
| 6,218,979 B1 | 4/2001 | Barnes et al. | |
| 6,289,238 B1 * | 9/2001 | Besson et al. | 600/509 |
| 6,292,688 B1 | 9/2001 | Patton | |
| 6,315,719 B1 * | 11/2001 | Rode et al. | 600/300 |
| 6,351,246 B1 | 2/2002 | McCorkle | |
| 6,454,708 B1 * | 9/2002 | Ferguson et al. | 600/300 |
| 6,466,125 B1 * | 10/2002 | Richards et al. | 340/573.4 |
| 6,489,893 B1 | 12/2002 | Fullerton et al. | |
| 6,492,906 B1 | 12/2002 | Richards et al. | |
| 6,524,239 B1 * | 2/2003 | Reed et al. | 600/300 |
| 6,608,910 B1 * | 8/2003 | Srinivasa et al. | 382/100 |
| 6,611,206 B2 * | 8/2003 | Milanski et al. | 340/573.1 |
| 6,611,783 B2 * | 8/2003 | Kelly et al. | 702/150 |
| 6,656,116 B2 * | 12/2003 | Kim et al. | 600/300 |
| 6,661,345 B1 * | 12/2003 | Bevan et al. | 340/575 |
| 6,696,957 B2 * | 2/2004 | Shepher | 340/573.1 |
| 6,730,023 B1 * | 5/2004 | Dodds | 600/300 |
| 6,753,780 B2 * | 6/2004 | Li | 340/573.1 |
| 6,950,022 B2 | 9/2005 | Breed | |
| 6,954,145 B2 | 10/2005 | Nakamura et al. | |
| 7,001,334 B2 * | 2/2006 | Reed et al. | 600/300 |
| 7,106,885 B2 * | 9/2006 | Osterweil et al. | 382/103 |
| 7,196,629 B2 * | 3/2007 | Ruoss et al. | 340/573.1 |
| 7,272,431 B2 * | 9/2007 | McGrath | 600/509 |
| 7,417,581 B2 | 8/2008 | Fullerton et al. | |
| 7,525,434 B2 | 4/2009 | Batra | |
| 7,567,200 B1 * | 7/2009 | Osterweil | 342/28 |
| 7,692,573 B1 * | 4/2010 | Funk | 342/90 |
| 7,916,066 B1 * | 3/2011 | Osterweil | 342/28 |
| 8,068,051 B1 * | 11/2011 | Osterweil | 342/28 |
| 8,094,009 B2 * | 1/2012 | Allen et al. | 340/539.12 |
| 8,125,331 B2 * | 2/2012 | Allen et al. | 340/539.12 |
| 8,130,095 B2 * | 3/2012 | Allen et al. | 340/539.12 |
| 8,204,786 B2 * | 6/2012 | LeBoeuf et al. | 705/14.66 |
| 8,284,046 B2 * | 10/2012 | Allen et al. | 340/539.12 |
| 8,284,990 B2 * | 10/2012 | Ma et al. | 382/103 |
| 8,311,616 B2 * | 11/2012 | Feldman et al. | 600/430 |
| 8,577,446 B2 * | 11/2013 | Kyle et al. | 600/473 |
| 2003/0033449 A1 | 2/2003 | Frantz et al. | |
| 2003/0058372 A1 | 3/2003 | Williams et al. | |
| 2003/0135097 A1 * | 7/2003 | Wiederhold et al. | 600/301 |
| 2004/0027270 A1 * | 2/2004 | Fullerton et al. | 342/28 |
| 2004/0249257 A1 * | 12/2004 | Tupin et al. | 600/407 |
| 2004/0249258 A1 * | 12/2004 | Tupin et al. | 600/407 |
| 2005/0015286 A1 * | 1/2005 | Rudnik et al. | 705/7 |
| 2005/0040230 A1 * | 2/2005 | Swartz et al. | 235/383 |
| 2005/0046584 A1 | 3/2005 | Breed | |
| 2005/0163302 A1 | 7/2005 | Mock et al. | |
| 2006/0001545 A1 * | 1/2006 | Wolf | 340/573.1 |
| 2006/0061504 A1 * | 3/2006 | Leach et al. | 342/22 |
| 2006/0218244 A1 | 9/2006 | Rasmussen et al. | |
| 2006/0224051 A1 | 10/2006 | Teller et al. | |
| 2006/0239471 A1 * | 10/2006 | Mao et al. | 381/92 |
| 2007/0121097 A1 | 5/2007 | Boillot | |
| 2007/0136774 A1 * | 6/2007 | Lourie et al. | 725/105 |
| 2007/0149282 A1 | 6/2007 | Lu et al. | |
| 2007/0214371 A1 | 9/2007 | You et al. | |
| 2008/0007445 A1 | 1/2008 | Leach, Jr. et al. | |
| 2008/0021401 A1 | 1/2008 | Jacobsen et al. | |
| 2008/0028206 A1 | 1/2008 | Sicard et al. | |
| 2008/0065468 A1 | 3/2008 | Berg et al. | |
| 2008/0077015 A1 * | 3/2008 | Boric-Lubecke et al. | 600/453 |
| 2008/0098448 A1 * | 4/2008 | Mondesir et al. | 725/126 |
| 2008/0101329 A1 * | 5/2008 | Richards et al. | 370/347 |
| 2008/0146892 A1 | 6/2008 | LeBoeuf et al. | |
| 2008/0165046 A1 * | 7/2008 | Fullerton et al. | 342/21 |
| 2008/0167535 A1 | 7/2008 | Stivoric et al. | |
| 2008/0183090 A1 | 7/2008 | Farringdon et al. | |
| 2008/0240379 A1 | 10/2008 | Maislos et al. | |
| 2008/0270172 A1 * | 10/2008 | Luff et al. | 705/1 |
| 2008/0270238 A1 | 10/2008 | Zweben et al. | |
| 2009/0017910 A1 * | 1/2009 | Rofougaran et al. | 463/36 |
| 2009/0025024 A1 | 1/2009 | Beser et al. | |
| 2009/0052859 A1 * | 2/2009 | Greenberger et al. | 386/46 |
| 2009/0138805 A1 * | 5/2009 | Hildreth | 715/745 |
| 2009/0140851 A1 * | 6/2009 | Graves et al. | 340/539.12 |
| 2009/0164287 A1 | 6/2009 | Kies et al. | |
| 2009/0284378 A1 * | 11/2009 | Ferren et al. | 340/573.1 |
| 2009/0296997 A1 | 12/2009 | Rocheford | |
| 2009/0328089 A1 | 12/2009 | Pradeep et al. | |
| 2010/0106475 A1 | 4/2010 | Smith et al. | |
| 2010/0117837 A1 * | 5/2010 | Stirling et al. | 340/573.1 |
| 2010/0234714 A1 | 9/2010 | Mercier et al. | |
| 2010/0234720 A1 | 9/2010 | Tupin, Jr. et al. | |
| 2010/0241313 A1 | 9/2010 | Fiske et al. | |
| 2010/0259395 A1 * | 10/2010 | Nuthi | 340/573.1 |
| 2010/0306388 A1 * | 12/2010 | Newville | 709/227 |
| 2011/0080529 A1 * | 4/2011 | Wong | 348/734 |
| 2011/0109545 A1 | 5/2011 | Touma et al. | |
| 2011/0161136 A1 * | 6/2011 | Faith et al. | 705/7.29 |
| 2011/0307210 A1 | 12/2011 | Stevens et al. | |
| 2012/0116186 A1 | 5/2012 | Shrivastav et al. | |
| 2012/0286955 A1 * | 11/2012 | Welch et al. | 340/573.1 |
| 2012/0326873 A1 * | 12/2012 | Utter, II | 340/573.1 |

OTHER PUBLICATIONS

PCT International Search Report; International App. No. PCT/US11/00018; Mar. 4, 2011; pp. 1-2.

Michahelles et al.; "Less Contact: Heart-rate detection without even touching the user"; Proceedings of the Eighth International Symposium on Wearable Computers; 2004; vol. 1; pp. 1-4; Retrieved from URL: http://ieeexplore.ieee.org/stamp/stamp.jsp?tp=&arnumber=1364682&isnumber=29895 printed on Dec. 26, 2011; IEEE.

PCT International Search Report; International App. No. PCT/ US 11/01629; Jan. 9, 2012; pp. 1-3.

PCT International Search Report; International App. No. PCT/US 11/01789; Feb. 14, 2012; pp. 1-2.

PCT International Search Report; International App. No. PCT/US 11/00019; Mar. 14, 2011; pp. 1-2.

(56) References Cited

OTHER PUBLICATIONS

Azevedo et al.; "Micropower Impulse Radar"; Science and Technology Review; Jan./Feb. 1996; Retrieved from the internet on Feb. 10, 2012 (as provided by Officer); pp. 16-29; located at: https://www.llnl.gov/str/pdfs/01_96.2.pdf.

PCT International Search Report; International App. No. PCT US2011/001985; May 2, 2012; pp. 1-5.

Tivive et al.; "A Human Gait Classification Method Based on Radar Doppler Spectrograms"; EURASIP Journal on Advances in Signal Processing; Bearing a date of Feb. 1, 2010; pp. 1-12; vol. 2010; Hindawi Publishing Corporation.

Warren et al.; "Designing Smart Health Care Technology into the Home of the Future"; Sandia National Laboratories; Mar. 25, 1999; pp. 1-18.

Zhang, Zhaonian; "A Micro-Doppler Sonar for Acoustic Surveillance in Sensor Networks"; ProQuest Dissertations and Theses: The Science and Engineering Collection; bearing a date of Aug. 2008; 224 pgs.; ProQuest, LLC.

European Patent Office, Supplementary European Search Report, Pursuant to Rule 62 EPC; App. No. 11834761.6; Apr. 7, 2014 (received by our Agent on Apr. 22, 2014); pp. 1-6.

* cited by examiner

SURVEILLANCE OF STRESS CONDITIONS OF PERSONS USING MICRO-IMPULSE RADAR

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of the following United States Patent Applications:

Application Ser. No. 12/930,043, entitled METHOD AND APPARATUS FOR MEASURING THE MOTION OF A PERSON, naming Mahalaxmi Gita Bangera, Roderick A. Hyde, Muriel Y. Ishikawa, Edward K. Y. Jung, Jordin T. Kare, Eric C. Leuthardt, Nathan P. Myhrvold, Elizabeth A. Sweeney, Clarence T. Tegreene, David B. Tuckerman, Thomas A. Weaver, Lowell L. Wood, Jr., and Victoria Y. H. Wood as inventors, filed on Dec. 22, 2010, which is currently co-pending, or is an application of which a currently co-pending application is entitled to the benefit of the filing date;

Application Ser. No. 12/928,703, entitled TRACKING IDENTITIES OF PERSONS USING MICRO-IMPULSE RADAR, naming Mahalaxmi Gita Bangera, Roderick A. Hyde, Muriel Y. Ishikawa, Edward K. Y. Jung, Jordin T. Kare, Eric C. Leuthardt, Nathan P. Myhrvold, Elizabeth A. Sweeney, Clarence T. Tegreene, David B. Tuckerman, Thomas A. Weaver, Lowell L. Wood, Jr., and Victoria Y. H. Wood as inventors, filed on Dec. 16, 2010, which is currently co-pending, or is an application of which a currently co-pending application is entitled to the benefit of the filing date;

Application Ser. No. 12/925,407, entitled MEDIA OUTPUT WITH MICRO-IMPULSE RADAR FEEDBACK OF PHYSIOLOGICAL RESPONSE, naming Mahalaxmi Gita Bangera, Roderick A. Hyde, Muriel Y. Ishikawa, Edward K. Y. Jung, Jordin T. Kare, Eric C. Leuthardt, Nathan P. Myhrvold, Elizabeth A. Sweeney, Clarence T. Tegreene, David B. Tuckerman, Lowell L. Wood, Jr., and Victoria Y. H. Wood as inventors, filed on Oct. 20, 2010, which is currently co-pending, or is an application of which a currently co-pending application is entitled to the benefit of the filing date;

Application Ser. No. 12/924,036 entitled CONTROL OF AN ELECTRONIC APPARATUS USING MICRO-IMPULSE RADAR, naming Mahalaxmi Gita Bangera, Roderick A. Hyde, Muriel Y. Ishikawa, Edward K. Y. Jung, Jordin T. Kare, Eric C. Leuthardt, Nathan P. Myhrvold, Elizabeth A. Sweeney, Clarence T. Tegreene, David B. Tuckerman, Lowell L. Wood, Jr., and Victoria Y. H. Wood as inventors, filed on Sep. 17, 2010, which is currently co-pending, or is an application of which a currently co-pending application is entitled to the benefit of the filing date; and Application Ser. No. 12/655,808, entitled MICRO-IMPULSE RADAR DETECTION OF A HUMAN DEMOGRAPHIC AND DELIVERY OF TARGETED MEDIA CONTENT, naming Mahalaxmi Gita Bangera, Roderick A. Hyde, Muriel Y. Ishikawa, Edward K. Y. Jung, Jordin T. Kare, Eric C. Leuthardt, Nathan P. Myhrvold, Elizabeth A. Sweeney, Clarence T. Tegreene, David B. Tuckerman, Lowell L. Wood, Jr., and Victoria Y. H. Wood as inventors, filed on Jan. 5, 2010, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

According to an embodiment, a surveillance system can include a micro-impulse radar (MIR) configured to survey a region. A controller can be configured to receive an input signal from the MIR, extract from the signal one or more physical or physiological attributes corresponding to a predicted human stress condition, and output a notification signal.

According to an embodiment, a method for surveilling persons includes probing a region with a MIR to produce a MIR signal, decoding from the MIR signal physiological information corresponding to a person scanned by the MIR, and correlating the physiological information to a predicted stress condition. The method can include providing an indication of the predicted stress condition of the person.

According to an embodiment, a non-transient computer-readable medium can carry computer instructions configured to cause a computer to perform steps including probing a region with a MIR to produce a MIR signal, decoding from the MIR signal physiological information corresponding to a person scanned by the MIR, and correlating the physiological information to a predicted stress condition. The non-transient computer-readable instructions can also cause the computer to provide an indication of the predicted stress condition of the person.

According to an embodiment, a system configured to track a person exhibiting a stress condition can include a first MIR configured to probe a first region at least partially occupied by a person and produce first MIR data related to one or more first attributes of the person, and a first computer processing resource operatively coupled to the first MIR and configured to predict a stress condition of the person from the one or more first attributes of the person included in the first MIR data.

According to an embodiment, a method for tracking a person with a stress condition includes probing a person with a MIR to produce a MIR signal, analyzing the MIR signal to determine a predicted stress condition corresponding to the person, correlating the MIR signal with a video image of the person, and using video image processing to track the movements of the person with at least one video camera.

According to an embodiment, a non-transient computer-readable medium can carry computer instructions configured to cause a computer to perform steps including operating a MIR to probe a person to produce a MIR signal, analyzing the MIR signal to determine a predicted stress condition corresponding to the person, correlating the MIR signal with a video image of the person, and tracking the movements of the person with at least one video camera.

According to an embodiment, a system for evaluating a risk condition corresponding to a person can include a MIR configured to probe a plurality of persons to produce a MIR signal, a processor operatively coupled to the MIR and configured to determine one or more physiological parameters from each of the plurality of persons, and a computer operatively coupled to the processor and configured to receive the one or more physiological parameters, analyze the one or more physiological parameters, and indicate a person whose one or more physiological parameters are functionally related to the one or more physiological parameters of other persons.

According to an embodiment, a method for evaluating a risk condition corresponding to a person can include operating a MIR configured to probe a plurality of persons to produce a MIR signal, determining one or more physiological parameters from the MIR signal corresponding to each of the plurality of persons, analyzing the one or more physiological parameters, and indicating a person whose one or more physiological parameters are functionally related to the one or more physiological parameters of other persons.

According to an embodiment, a non-transient computer-readable medium can carry computer instructions configured to cause a computer to perform steps including operating a MIR configured to probe a plurality of persons to produce a MIR signal, determining one or more physiological parameters from the MIR signal corresponding to each of the plurality of persons, analyzing the one or more physiological parameters, and indicating a person whose one or more physiological parameters are functionally related to the one or more physiological parameters of other persons.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
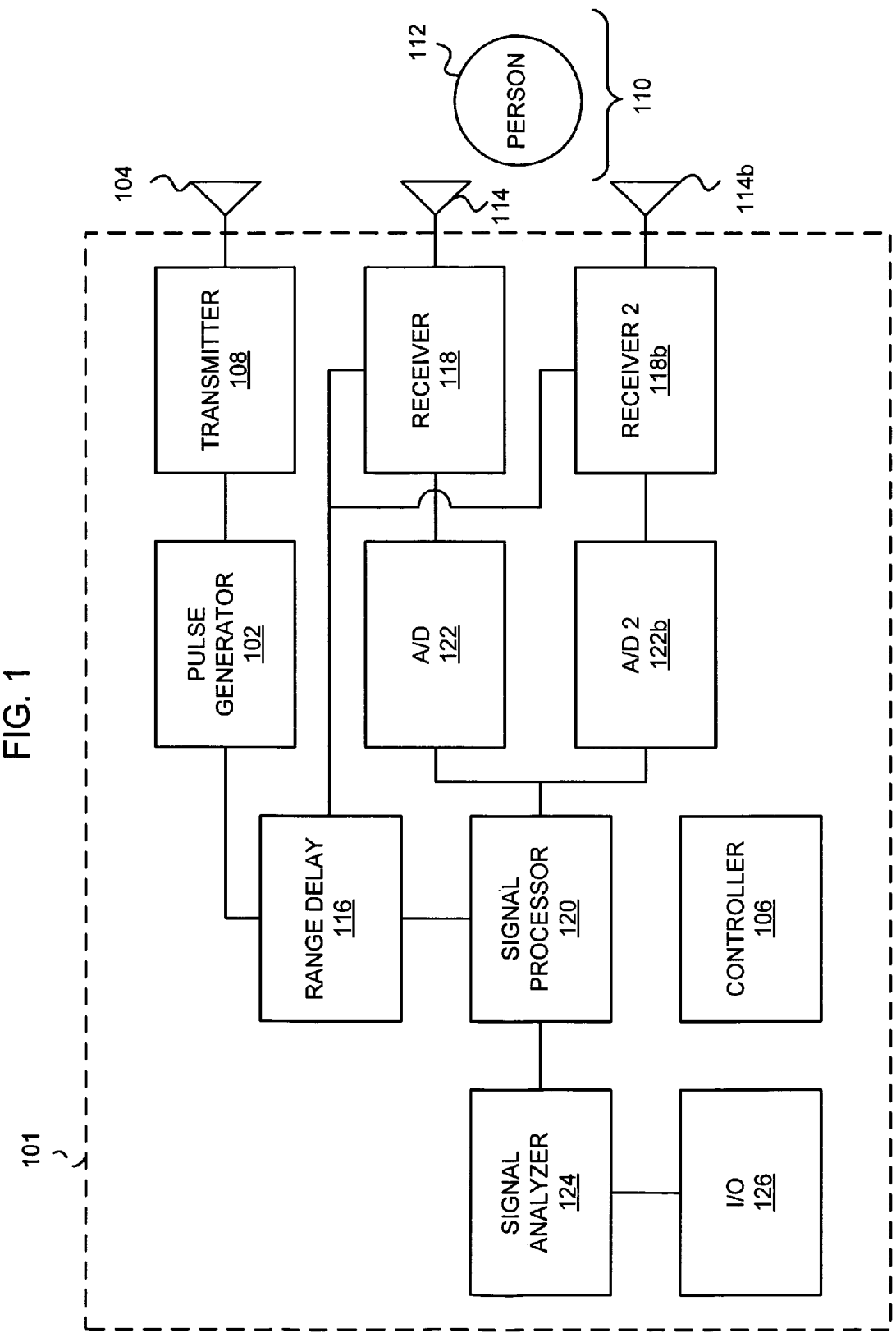
FIG. 1 is a simplified block diagram of a micro-impulse radar (MIR), according to an embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

FIG. 1 is a simplified block diagram of a micro-impulse radar (MIR) 101, according to an embodiment. A pulse generator 102 is configured to output a relatively short voltage pulse that is applied to a transmit antenna 104. A typical transmitted pulse width can be between about two hundred picoseconds and about 5 nanoseconds, for example. The voltage pulse can be conditioned and amplified (or attenuated) for output by a transmitter 108. For example, the transmitter 108 can transmit the voltage pulse or can further condition the pulse, such as by differentiating a leading and/or trailing edge to produce a short sub-nanosecond transmitted pulse. The voltage pulse is typically not modulated onto a carrier frequency. Rather, the voltage pulse transmission spectrum is the frequency domain transform of the emitted pulse. The MIR 101 can probe a region 110 by emitting a series of spaced voltage pulses. For example, the series of voltage pulses can be spaced between about 100 nanoseconds and 100 microseconds apart. Typically, the pulse generator 102 emits the voltage pulses with non-uniform spacing such as random or pseudo-random spacing, although constant spacing can be used if interference or compliance is not a concern. Spacing between the series of voltage pulses can be varied responsive to detection of one or more persons 112 in the region 110. For example, the spacing between pulses can be relatively large when a person 112 is not detected in the region 110. Spacing between pulses can be decreased (responsive to one or more commands from a controller 106) when a person 112 is detected in the region 110. For example, the decreased time between pulses can result in faster MIR data generation for purposes of more quickly determining information about one or more persons 112 in the region 110. The emitted series of voltage pulses can be characterized by spectral components having high penetration that can pass through a range of materials and geometries in the region 110.

An object 112 (such as a person) in the probed region 110 can selectively reflect, refract, absorb, and/or otherwise scatter the emitted pulses. A return signal including a reflected, refracted, absorbed, and/or otherwise scattered signal can be received by a receive antenna 114. Optionally, the receive antenna 114 and transmit antenna 104 can be combined into a single antenna. In a single antenna embodiment, a filter (not shown) can be used to separate the return signal from the emitted pulse.

A probed region 110 can be defined according to an angular extent and distance from the transmit antenna 104 and the receive antenna 114. Distance can be determined by a range delay 116 configured to trigger a receiver 118 operatively coupled to the receive antenna 114. For example, the receiver 118 can include a voltage detector such as a capture-and-hold capacitor or network. The range delay corresponds to distance into the region 110. Range delay can be modulated to capture information corresponding to different distances.

A signal processor 120 can be configured to receive detection signals or data from the receiver 118 and the analog to digital converter 122, and by correlating range delay to the detection signal, extract data corresponding to the probed region 110 including the object 112.

Optionally, the MIR 101 can include a second receive antenna 114b. The second receive antenna can be operatively coupled to a second receiver 118b coupled to an output of the range delay 116 or a separate range delay (not shown) configured to provide a delay selected for a depth into the region 110. The signal processor 120 can further receive output from a second A/D converter 122b operatively coupled to the second receiver 118b.

The signal processor 120 can be configured to compare detection signals received by the antennas 114, 114b. For example, the signal processor 120 can search for common signal characteristics such as similar reflected static signal strength or spectrum, similar (or corresponding) Doppler shift, and/or common periodic motion components, and compare the respective range delays corresponding to detection by the respective antennas 114, 114b. Signals sharing one or more characteristics can be correlated to triangulate to a location of one or more objects 112 in the region 110 relative to known locations of the antennas 114, 114b. The triangulated locations can be output as computed ranges of angle or computed ranges of extent.

For example, a first signal corresponding to a reflected pulse received by an antenna element 114 can be digitized by an analog-to-digital converter (A/D) 122 to form a first digitized waveform. A second signal corresponding to the reflected pulse received by a second antenna element 114b can similarly be digitized by and A/D 122b (or alternatively by the same A/D converter 122) to form a second digitized waveform. The signal processor 120 can compare the first and second digitized waveforms and deduce angular information from the first and second digitized waveforms and known geometry of the first and second antenna elements.

A second pulse can be received at a second range delay 116 value and can be similarly signal processed to produce a second set of angular information that maps a second surface at a different distance. Depth within a given range delay can be inferred from a strength of the reflected signal. A greater number of signals can be combined to provide additional depth information. A series of pulses can be combined to form a time series of signals corresponding to the object 112 that includes movement information of the object 112 through the region 110. The object 112 described herein can include one or more persons.

The signal processor 120 outputs MIR data. The MIR data can include object location information, object shape information, object velocity information, information about inclusion of high density and/or conductive objects such as jewelry, cell phones, glasses including metal, etc., and physiological information related to periodic motion. The MIR data can include spatial information, time-domain motion information, and/or frequency domain information. Optionally, the MIR data can be output in the form of an image. MIR data in the form of an image can include a surface slice made of pixels or a volume made of voxels. Optionally, the image can include vector information.

The MIR data from the signal processor 120 is output to a signal analyzer 124. The signal analyzer 124 can be integrated with the signal processor 120 and/or can be included in the same MIR 101, as shown. Alternatively, the signal processor 120 can output MIR data through an interface to a signal analyzer 124 included in an apparatus separate from the MIR 101.

A signal analyzer 124 can be configured to extract desired information from MIR data received from the signal processor 120. Data corresponding to the extracted information can be saved in a memory for access by a data interface 126 or can be pushed out the data interface 126.

The signal analyzer 124 can be configured to determine the presence of a person 112 in the region 110. For example, MIR data from the signal processor can include data having a static spectrum at a location in the region 110, and a periodic motion spectrum corresponding to the location characteristic of a human physiological process (e.g. heartbeat and/or breathing). From the correspondence of such MIR data, it can be deduced that a person 112 is at the location in the region 110. The signal analyzer 124 can be configured to determine a number of persons 112 in the region 110. The signal analyzer 124 can be configured to determine the size of a person and/or relative size of anatomical features of a person 112 in the region 110. The signal analyzer 124 can be configured to determine the presence of an animal 112 in the region 110. The signal analyzer 124 can be configured to determine movement and/or speed of movement of a person 112 through the region 110. The signal analyzer 124 can be configured to determine or infer the orientation of a person 112 such as the direction a person is facing relative to the region 110. The signal analyzer 124 can be configured to determine one or more physiological aspects of a person 112 in the region 110. The signal analyzer 124 can determine presence of a personal appliance such as a cell phone, PDA, etc. and/or presence of metalized objects such as credit cards, smart cards, access cards, etc. The signal analyzer 124 can infer the gender and age of one or more persons based on returned MIR data. For example, male bodies can generally be characterized by higher mass density than female bodies, and thus can be characterized by somewhat greater reflectivity at a given range. Adult female bodies can exhibit relatively greater harmonic motion ("jiggle") responsive to movements, and can thus be correlated to harmonic spectra characteristics. Older persons generally move differently than younger persons, allowing an age inference based on detected movement in the region 110.

By determination of one or more such aspects and/or combinations of aspects, the signal analyzer 124 can determine a demographic of one or more persons 112 in the region 110.

For example, MIR data can include movement corresponding to the beating heart of one or more persons 112 in the region 110. The signal analyzer 124 can filter the MIR data to remove information not corresponding to a range of heart rates, and determine one or more heart rates by comparing movement of the heart surface to the MIR signal rate. The one or more heart rates can further be characterized according to a confidence factor, depending on statistical certainty regarding the determined one or more heart rates.

Similarly, the signal analyzer 124 can determine one or more respiration rates by measuring movement corresponding to the chest or diaphragm of one or more persons 112. The signal analyzer 124 can determine movement, a direction of movement, and/or a rate of movement of one or more persons 112 in the region 110. Operation of the signal analyzer 124 is described in greater detail below by reference to FIGS. 2 and 3.

An electronic controller 106 can be operatively coupled to the pulse generator 102, the transmitter 108, the range delay 116, the receiver 118, the analog-to-digital converter 122, the signal processor 120, and/or the signal analyzer 124 to control the operation of the components of the MIR 101. For embodiments so equipped, the electronic controller 106 can also be operatively coupled to the second receiver 118b, and the second analog-to-digital converter 122b. The data interface 126 can include a high speed interface configured to output data from the signal analyzer 124. Alternatively, for cases where signals are analyzed externally to the MIR, the data interface 126 can include a high speed interface configured to output MIR data from the signal processor 120. The data interface 126 can include an interface to the controller 106. Optionally, the controller 106 can be interfaced to external systems via a separate interface (not shown).

Figure 2:
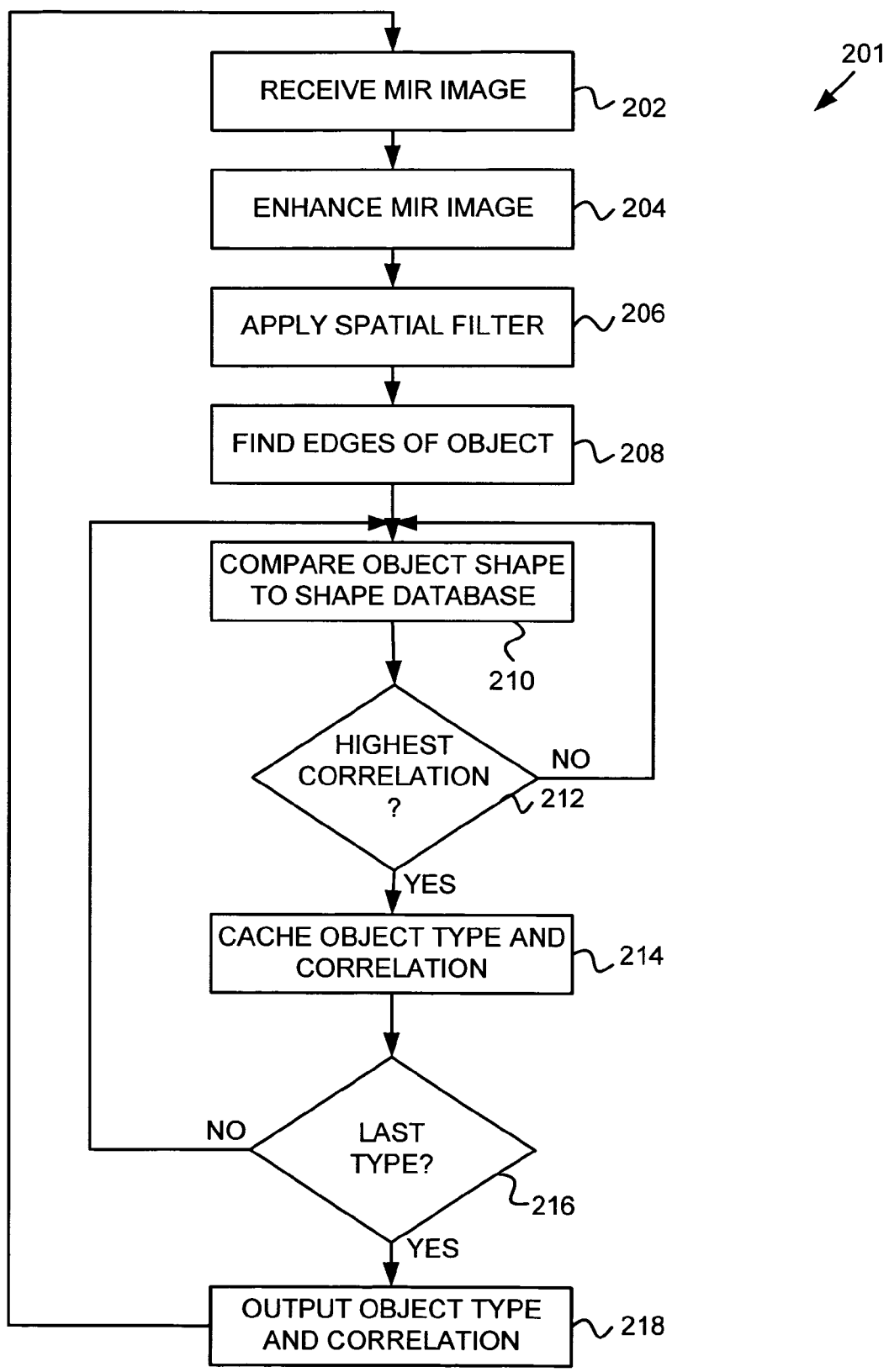
FIG. 2 is a flow chart showing an illustrative process for determining the presence of a person in a region with the MIR of FIG. 1, according to an embodiment.

FIG. 2 is a flow chart showing an illustrative process 201 for determining the presence of one or more persons 112 in the region 110 with the signal analyzer 124 of the MIR 101, according to an embodiment. Beginning with step 202, MIR data is received as described above in conjunction with FIG. 1. The MIR data can correspond to a plurality of probes of the region 110. Proceeding to optional step 204, the MIR data can be enhanced to facilitate processing. For example, grayscale data corresponding to static reflection strength as a function of triangulated position can be adjusted, compressed, quantized, and/or expanded to meet a desired average signal brightness and range. Additionally or alternatively, velocity information corresponding to Doppler shift, and/or frequency transform information corresponding to periodically varying velocity can similarly be adjusted, compressed, quantized, and/or expanded. Systematic, large scale variations in brightness can be balanced, such as to account for side-to-side variations in antenna coupling to the region. Contrast can be enhanced such as to amplify reflectance variations in the region.

Proceeding to optional step 206, a spatial filter can be applied. Application of a spatial filter can reduce processing time and/or capacity requirements for subsequent steps described below. The spatial filter may, for example, include a computed angle or computed extent filter configured to remove information corresponding to areas of contrast, velocity, or frequency component(s) having insufficient physical extent to be large enough to be an object of interest. The spatial filter may, for example, identify portions of the region 110 having sufficient physical extent to correspond to body parts or an entire body of a person 112, and remove features corresponding to smaller objects such as small animals, leaves of plants, or other clutter. According to an embodiment, the spatial filter can remove information corresponding to areas of contrast, velocity, or frequency component(s) having physical extent greater than a maximum angle or extent that is likely to correspond to a person or persons 112. In other embodiments, the spatial filter applied in step 206 can eliminate small, low contrast features, but retain small, high contrast features such as jewelry, since such body ornamentation can be useful in some subsequent processes. The step of applying the spatial filter 206 can further include removing background features from the MIR data. For example, a wall lying between an antenna 104, 114 and the region 110 can cast a shadow such as a line in every MIR signal. Removal of such constant features can reduce subsequent processing requirements.

Proceeding to optional step 208, an edge-finder can identify edges of objects 112 in the region 110. For example, a global threshold, local threshold, second derivative, or other algorithm can identify edge candidates. Object edges can be used, for example, to identify object shapes, and thus relieve subsequent processes from operating on grayscale data. Alternatively, step 208 can be omitted and the process of identifying objects can be performed on the grayscale MIR data.

Proceeding to step 210, processed data corresponding to the MIR data is compared to a database to determine a match. The object data received from step 202 (and optionally steps 204, 206, and/or 208) can be compared to corresponding data for known objects in a shape database. Step 210 can be performed on a grayscale signal, but for simplicity of description it will be assumed that optional step 208 was performed and matching is performed using object edges, velocity, and/or spectrum values. For example, the edge of an object 112 in the region 110 can include a line corresponding to the outline of the head and torso, cardiac spectrum, and movements characteristic of a young adult male. A first shape in the shape database can include the outline of the head and torso, cardiac spectrum, density, and movements characteristic of a young adult female and/or the head and torso outline, cardiac spectrum, density, and movements characteristic of a generic human. The differences between the MIR data and the shape database shape can be measured and characterized to derive a probability value. For example, a least-squares difference can be calculated.

Optionally, the object shape from the MIR data can be stepped across, magnified, and stepped up and down the shape database data to minimize a sum-of-squares difference between the MIR shape and the first shape in the shape database. The minimum difference corresponds to the probability value for the first shape.

Proceeding to step 212, if the probability value for the first shape is the best probability yet encountered, the process proceeds to step 214. For the first shape tested, the first probability value is the best probability yet encountered. If an earlier tested shape had a higher probability to the MIR data, the process loops back from step 212 to step 210 and the fit comparison is repeated for the next shape from the shape database.

In step 214, the object type for the compared shape from the shape database and the best probability value for the compared shape are temporarily stored for future comparison and/or output. For example, the compared shape from the shape database can be identified by metadata that is included in the database or embedded in the comparison data. Proceeding to step 216, the process either loops back to step 210 or proceeds to step 218, depending on whether a test is met. If the most recently compared shape is the last shape available for comparison, then the process proceeds to step 218. Optionally, if the most recently compared shape is the last shape that the process has time to compare (for example, if a new MIR data is received and/or if another process requires output data from the process 201) then the process proceeds to step 218. In step 218, the object type and the probability value is output. The process can then loop back to step 202 and the process 201 can be repeated.

Otherwise, the process 201 loops from step 216 back to step 210. Again, in step 210, the next comparison shape from a shape database is loaded. According to an embodiment, the comparison can proceed from the last tested shape in the shape database. In this way, if the step 218 to 202 loop occurs more rapidly than all objects in the shape database can be compared, the process eventually works its way through the entire shape database. According to an embodiment, the shape database can include multiple copies of the same object at different orientations, distances, and positions within the region. This can be useful to reduce processing associated with stepping the MIR shape across the shape database shape and/or changing magnification.

The object type can include determination of a number of persons 112 in the region 110. For example, the shape database can include outlines, cardiac and/or respiration spectra, density, and movement characteristics for plural numbers of persons. According to embodiments, the shape library can include shapes not corresponding to persons. This can aid in identification of circumstances where no person 212 is in the region 210. Optionally, process 201 can be performed using plural video frames such as averaged video frames or a series of video frames. Optionally, steps 212, 214, and 216 can be replaced by a single decision step that compares the probability to a predetermined value and proceeds to step 218 if the probability meets the predetermined value. This can be useful, for example, in embodiments where simple presence or absence of a person 212 in the region 210 is sufficient information.

According to an embodiment, the signal analysis process 201 of FIG. 2 can be performed using conventional software running on a general-purpose microprocessor. Optionally, the process 201 can use various combinations of hardware, firmware, and software; and can include the use of a digital signal processor.

Figure 3:
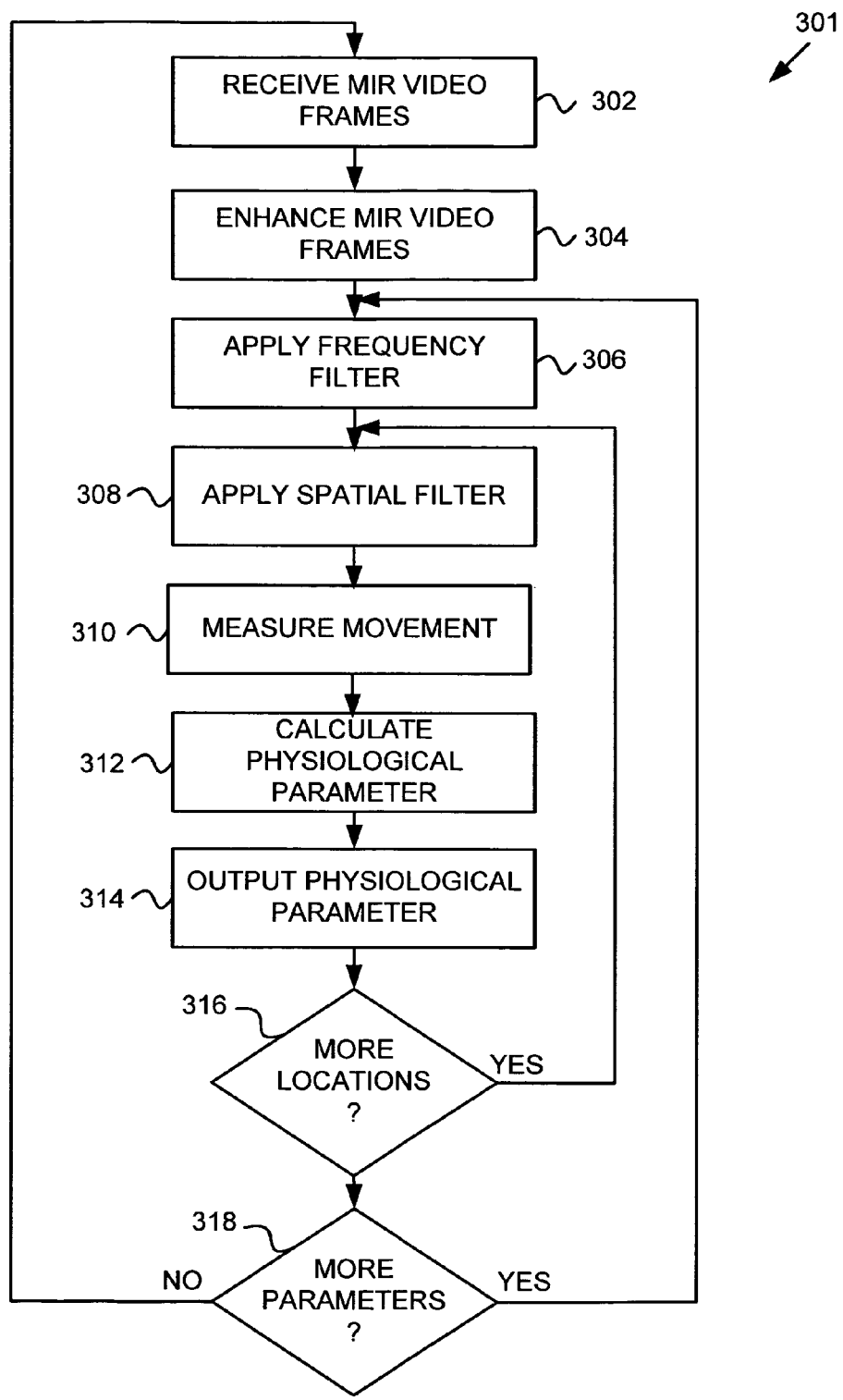
FIG. 3 is a flow chart showing an illustrative process for determining a physiological parameter of a person in a region with the MIR of FIG. 1, according to an embodiment.

FIG. 3 is a flow chart showing an illustrative process 301 for determining one or more particular physiological parameters of a person 112 in the region 110 with the signal analyzer 124 of the MIR 101, according to an embodiment. Optionally, the process 301 of FIG. 3 can be performed conditional to the results of another process such as the process 201 of FIG. 2. For example, if the process 201 determines that no person 112 is in the region 110, then it can be preferable to continue to repeat process 201 rather than execute process 301 in an attempt to extract one or more particular physiological parameters from a person that is not present.

Beginning with step 302, a series of MIR time series data is received. While the received time series data need not be purely sequential, the process 301 generally needs the time series data received in step 302 to have a temporal capture relationship appropriate for extracting time-based information. According to an embodiment, the MIR time series data can have a frame rate between about 16 frames per second and about 120 frames per second. Higher capture rate systems can benefit from depopulating frames, such as by dropping every other frame, to reduce data processing capacity requirements.

Proceeding to step 304, the MIR video frames can be enhanced in a manner akin to that described in conjunction with step 204 of FIG. 2. Optionally, step 304 can include averaging and/or smoothing across multiple MIR time series data. Proceeding to optional step 306, a frequency filter can be applied. The frequency filter can operate by comparing changes between MIR time series data to a reference frequency band for extracting a desired physical parameter. For example, if a desired physiological parameter is a heart rate, then it can be useful to apply a pass band for periodic movements having a frequency between about 20 cycles per minute and about 200 cycles per minute, since periodic motion beyond those limits is unlikely to be related to a human heart rate. Alternatively, step 304 can include a high pass filter that removes periodic motion below a predetermined limit, but retains higher frequency information that can be useful for determining atypical physiological parameters.

Proceeding to optional step 308, a spatial filter can be applied. The spatial filter may, for example, include a pass band filter configured to remove information corresponding to areas of contrast having insufficient physical extent to be large enough to be an object of interest, and remove information corresponding to areas too large to be an object of interest. The spatial filter may, for example, identify portions of the region 110 having sufficient physical extent to correspond to the heart, diaphragm, or chest of a person 112, and remove signal features corresponding to smaller or larger objects. The step of applying the spatial filter 308 can further include removing background features from the MIR data. For example, a wall lying between an antenna 104, 114 (114b) and the region 110 can cast a shadow such as a line in every instance of MIR data. Removal of such constant features can reduce subsequent processing requirements.

Proceeding to step 310, movement such as periodic movement in the MIR time series data is measured. For example, when a periodic motion is to be measured, a time-to-frequency domain transform can be performed on selected signal elements. For example, when a non-periodic motion such as translation or rotation is to be measured, a rate of movement of selected signal elements can be determined. Optionally, periodic and/or non-periodic motion can be measured in space vs. time. Arrhythmic movement features can be measured as spread in frequency domain bright points or can be determined as motion vs. time. Optionally, subsets of the selected signal elements can be analyzed for arrhythmic features. Optionally, plural subsets of selected signal elements can be cross-correlated for periodic and/or arrhythmic features. Optionally, one or more motion phase relationships between plural subsets of selected signal features, between a subset of a selected signal feature and the signal feature, or between signal features can be determined.

For example, a person with a hiccup can be detected as a non-periodic or arrhythmic motion superimposed over periodic motion of a signal element corresponding to the diaphragm of the person.

Proceeding to step 312, a physiological parameter can be calculated. For example, MIR data can include data having a periodic motion spectrum corresponding to the location characteristic of a human physiological process (e.g. heartbeat and/or breathing). Step 312 can include determining one or more heart rates by comparing movement of the heart surface to the MIR signal rate. The one or more heart rates can further be characterized according to a confidence factor, depending on statistical certainty regarding the determined one or more heart rates. Similarly, step 312 can include determining one or more respiration rates by measuring movement corresponding to the chest or diaphragm of one or more persons.

Proceeding to step 314, the physiological parameter can be output. Proceeding to step 316, if there are more locations to measure, the process 301 can loop back to execute step 308. If there are not more locations to measure, the process can proceed to step 318. In step 318, if there are more physiological parameters to measure, the process 301 can loop back to execute step 306. If there are not more physiological parameters to measure, the process 301 can loop back to step 302, and the process 301 of FIG. 3 can be repeated.

Figure 4:
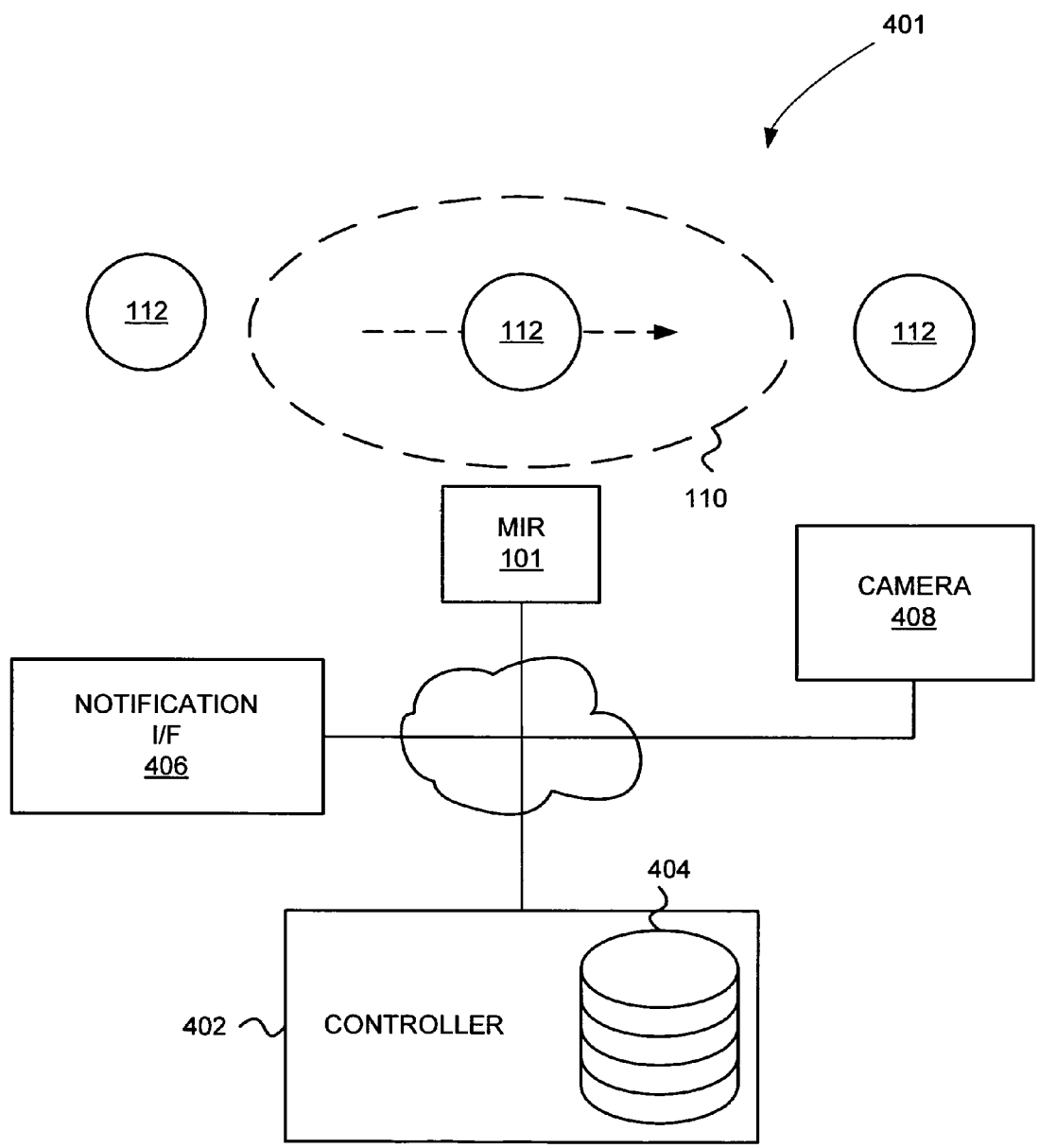
FIG. 4 is a block diagram of a surveillance system, according to an embodiment.

FIG. 4 is a block diagram of a surveillance system 401, according to an embodiment. The surveillance system 401 can include a MIR 101 configured to survey a region 110. The region 110 can be at least intermittently occupied by one or more persons 112. A controller 402 can be configured to receive an input signal from the MIR 101, extract from the signal one or more physical or physiological attributes corresponding to a predicted human stress condition, and output a notification signal.

The region 110 can include a region that is occupied by a succession of persons 112. For example, the region 110 can include a security checkpoint in a publically accessible area. Alternatively, the region 110 can be in a limited access or private area. For example, the system 401 can be used to provide primary monitoring of persons passing through a security checkpoint, or can be used to provide secondary monitoring, for example of persons who have already passed through a physical-based security checkpoint. Some examples of regions 110 include an airport security checkpoint, a security checkpoint at a federal building, an entry point to a military demarcation zone, a lobby of a bank, a vicinity of an automated teller machine, a store shoplifting deterrent region, an area prone to vandalism, an area prone to theft, a parking lot, a hospital, a retail store, a gas station, a restaurant or bar, a club, a school, a home, a business, an entertainment facility, or a sports facility.

The surveillance system 401 can operate by using the MIR 101 to probe the person(s) 112 in the region 110 to detect one or more physical or physiological attributes of the person(s). This can include one or more physical and one or more physiological attributes. For example, one or more physical attributes can include one or more of body size, body mass, height, body shape, posture, body permittivity, carried or otherwise associated articles (such as a pushed cart, wheelchair, or other non-carried but associated article), detectable body ornamentation, or body movements. One or more physiological attributes can include one or more of heart rate, respiration rate, heart anomaly, respiration anomaly, magnitude of heartbeat, magnitude of respiration, a rate or magnitude of inhalation, a rate or magnitude of exhalation, a tremor of all or part of a body, intracyclic characteristic of a heartbeat, intracyclic characteristic of respiration, or digestive muscle activity. The human stress condition can be predicted from the physical and/or physiological attributes.

As will be described below, the system 401 can be used to identify and/or deter persons 112 that have a probability of being in the process and/or having an intent to commit a crime or an act of terrorism; or in some cases, that have a probability of lying. Alternatively, the system can be used to identify persons 112 that have a probability of requiring aid or assistance, such as may be the case if a person exhibits a stress condition corresponding to physical distress. In the case of the former, a person 112 may stand out from other, innocent persons 112 by nervousness that is betrayed by fidgeting, increased heart rate, increased breathing rate, shallower breathing, decreased digestive muscle activity, etc. The system 401 can use the MIR 101 to detect these and other telltale symptoms that, while not necessarily visible to a camera or direct observation, can be detected by the MIR 101. The MIR 101 can also be used detect the presence of a weapon.

Whether or not stress symptoms exhibited by a person are characterized as unusual can be context-dependent. For example, people waiting to get through airport security may, as a population, tend to exhibit somewhat higher stress than persons waiting in line at a bank. The controller 402 can be further configured to receive or determine a range of the one or more physical or physiological attributes corresponding to normal range of human stress conditions in the region 110. For example, the controller 402 can include a non-transient computer-readable medium 404 configured to hold one or more physical or physiological attributes corresponding to a normal range of human stress conditions. The controller 402 can be configured to determine a range of the one or more physical or physiological attributes corresponding to a normal range of human stress conditions as a function of previously or later extracted one or more physical or physiological attributes. The controller 402 can be configured to determine, from previously or later extracted physical or physiological attributes, a range of one or more physical or physiological attributes corresponding to one or more anomalous human stress conditions, e.g., physiological and/or physical attributes that correspond to a risk condition.

The controller 402 can thus determine if the predicted human stress condition is anomalous compared to a normal range of human stress conditions in the region 110. For example, the controller 402 can determine that the predicted human stress condition is anomalous if the one or more physical or physiological attributes is (are) one or more standard deviations from an average value of the one or more physical or physiological attributes for persons 112 in the region 110. Alternatively, the predicted human stress condition can be considered anomalous if a combination of the one or more physical or physiological attributes is two or more standard deviations, or three or more standard deviations from an average value of the one or more physical or physiological attributes. Other functional relationships are contemplated.

The controller 402 can be configured to determine if the predicted human stress condition is anomalous and determine whether to output the notification signal as a function of the predicted human stress condition anomaly. The notification signal can be output via a notification interface 406 operatively coupled to the controller 402. For example, the notification interface 406 can include a computer display. In some embodiments, the notification interface 406 can be configured to notify a person having a view of the region 110. In one example, the notification interface 406 can include an interface configured to project an optical designation onto or near a person exhibiting an anomalous predicted stress condition. For example, such a person may be illuminated with a spotlight, a visible laser dot, or an infrared laser dot configured to be detected by a person wearing infrared vision goggles. Optionally, the notification interface can include an apparatus configured to notify a person exhibiting an anomalous predicted stress condition. For example, the notification interface can include a computer display aimed at the region that can notify a person suffering from anomalous health-related stress of the situation, so that the person may alter his/her behavior to recover or call for aid. In another example, the notification interface can include a computer display aimed at the region that can notify a person that his/her stress has been detected, thus acting as a deterrent to crime or heightening the stress to aid in a certainty of detection. Alternatively, the person notified by the notification interface 406 can be located relatively remotely and may not have a view of the region 110. Such a person can include, for example, a guard, a police officer, a civil servant, a military officer or enlisted person, or a healthcare professional.

The surveillance system 401 can include a camera 408 operatively coupled to the controller 402 and configured to capture a still or video image of a person 112 probed by the MIR 101. The controller is further configured to display the still or video image of the person probed by the micro-impulse radar via a notification interface. The controller 402 can be configured to output to a computer display 406 an image of the person 112 in the region 110 and a corresponding indicator of the predicted human stress condition corresponding to the person 112 in the region 110. This can be especially useful, for example, in applications where a system monitoring authority (e.g., a guard, police officer, civil servant, military officer or enlisted person, or healthcare professional that monitors the output of the system 401) (not shown) is located relatively remotely and may not have a view of the region 110.

As indicated above, the controller 402 can be configured to determine a risk or threat condition corresponding to the predicted human stress condition. For example, the predicted human stress condition can be used as a predictor of an intent to commit a crime or perform an act of terrorism. The controller can be configured to determine whether to output the notification signal as a function of time of day, a security threat status, or a security clearance status of the person in the region. Optionally, as described elsewhere herein, the determination of whether to output the notification signal can also be made in conjunction with determining an identity of a person, and determining a risk or threat condition and/or the predicted human stress condition as a function of a normal range of physical or physiological attributes of the person.

According to an embodiment, the controller 402 can be configured to predict the human stress condition by performing a statistical analysis of similarities between the one or more extracted physical or physiological attributes and one or more predetermined ranges of anomalous human stress conditions. Alternatively or additionally, the controller 402 can be configured to predict the human stress condition by performing a statistical analysis of similarities between the one or more extracted physical or physiological attributes and one or more predetermined ranges of normal human stress conditions. Alternatively or additionally, the controller 402 can be configured to predict the human stress condition by performing a statistical analysis of differences between the one or more extracted physical or physiological attributes and one or more predetermined ranges of normal human stress conditions. Alternatively or additionally, the controller 402 can be configured to predict the human stress condition by performing a statistical analysis of similarities between the one or more extracted physical or physiological attributes and one or more predetermined ranges of normal human stress conditions. Alternatively or additionally, the controller 402 can be configured to predict the human stress condition by performing a statistical analysis to identifying unusual stress conditions according to a joint fit of the extracted one or more physical or physiological attributes of a plurality of persons.

The surveillance system 401 can include at least one housing configured to disguise the presence of at least one of the MIR 101 or the controller 402, or signage (not shown) configured to alert a person in the region to the presence of the system 401. The surveillance system 401 can include a turnstile configured to admit a person 112 into the region 110, a barrier configured to prevent unauthorized movement around the region 110, or a barrier configured to protect bystanders from actions of person 112 in the region 110.

As indicated above, the predicted stress condition can correspond to high anxiety, and the notification signal can be output to a security authority. Alternatively, the predicted stress condition can correspond to physical distress, and the notification signal can be output to one or more persons selected to render aid or assistance.

Figure 5:
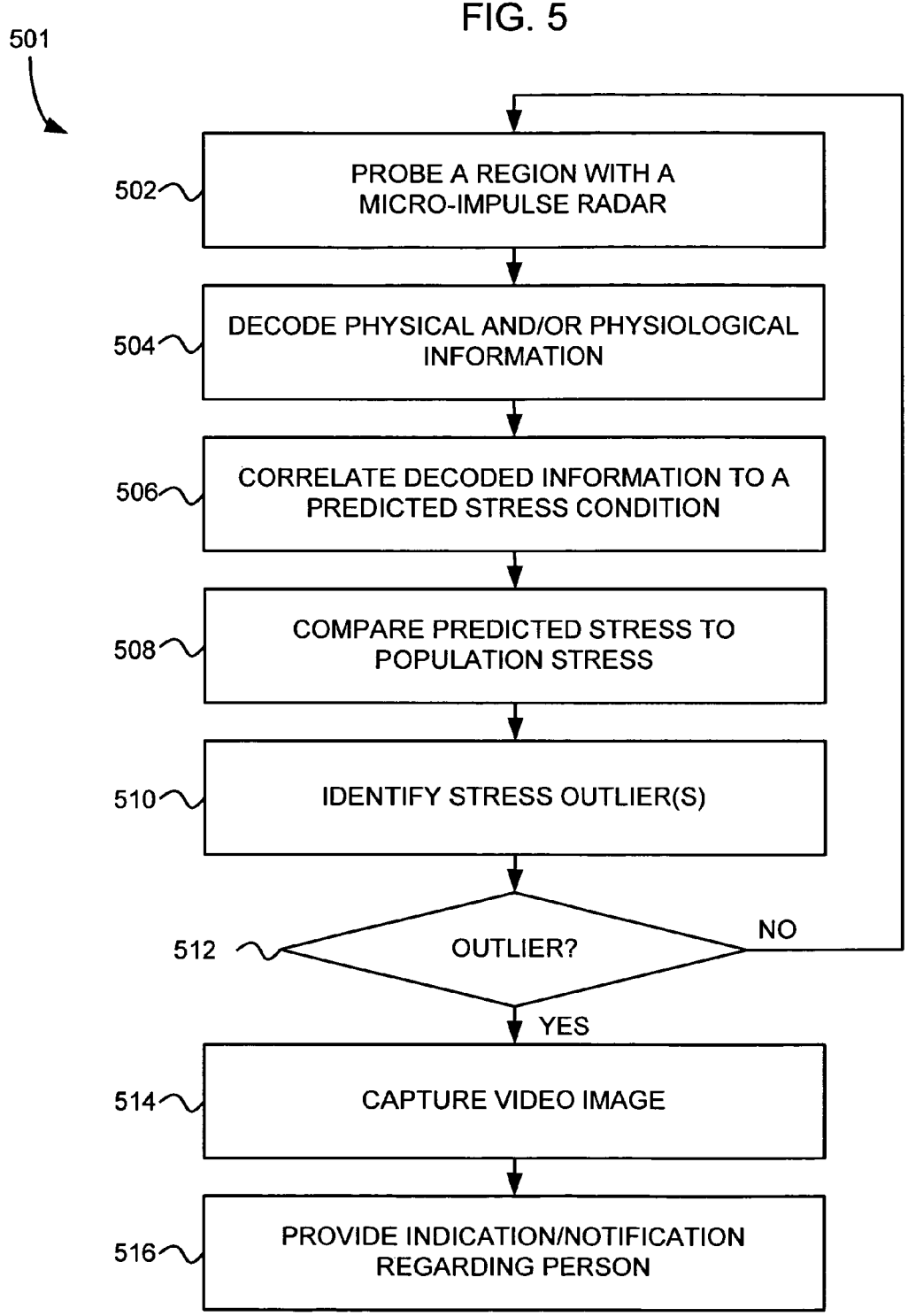
FIG. 5 is a flow chart showing a method for surveilling persons, according to an embodiment.

FIG. 5 is a flow chart showing a method 501 for surveilling persons, according to an embodiment. For example, the method of FIG. 5 can be executed by an embodiment of the surveillance system 401 shown in block diagram form in FIG. 4. Beginning at step 502, a region is probed a MIR to produce a MIR signal. As described above, the region can include a public region temporarily occupied by a succession of persons, such as a security checkpoint. According to examples, the region can include an airport security checkpoint, a security checkpoint at a federal building, an entry point to a military demarcation zone, a lobby of a bank, a vicinity of an automated teller machine, a store shoplifting deterrent region, an area prone to vandalism, an area prone to theft, a parking lot, a hospital, a retail store, a gas station, a restaurant or bar, a club, a school, a home, a business, an entertainment facility, or a sports facility.

Proceeding to step 504, the MIR signal is decoded to produce physiological information corresponding to a person scanned by the MIR. The physiological information can include one or more of heart rate, respiration rate, heart anomaly, respiration anomaly, magnitude of heartbeat, magnitude of respiration, a rate or magnitude of inhalation, a rate or magnitude of exhalation, a tremor of all or part of a body, intracyclic characteristic of a heartbeat, intracyclic characteristic of respiration, or digestive muscle activity. Step 504 can optionally include decoding one or more physical attributes corresponding to the person scanned by the MIR. For example, one or more physical attributes can include one or more of body size, body mass, height, body shape, posture, body permittivity, carried articles, or detectable body ornamentation, or body movements.

Proceeding to step 506, the physiological information (and optionally, physical information) is correlated to a predicted stress condition. For example, the decoded physiological information (and optionally, physical information) can be input to a look-up table (LUT) or formulated as a database query, and the LUT or database engine can respond with a numerical, graphical, or descriptive response corresponding to the predicted stress condition.

Correlating the physiological information to a predicted stress condition in step 506 can include performing a statistical analysis of similarities the decoded physiological information to one or more previously determined ranges of physiological information. For example, correlating the physiological information to a predicted stress condition includes performing a statistical analysis of differences between the decoded physiological information and one or more previously determined ranges of physiological information. Optionally, correlating the physiological information to a predicted stress condition includes performing a statistical analysis to maximize similarities or minimize differences according to a joint fit of a plurality of decoded physiological information to physiological information corresponding to a plurality of human stress conditions.

The process 501 can proceed to optional step 508, where a range of the physiological information corresponding to normal range of human stress conditions in the region can be received or determined. For example, this can include determining the normal range of human stress conditions as a function of previously extracted physiological information. Step 508 can also include determining, from previously extracted physiological information, one or more ranges of the physiological information corresponding to one or more anomalous human stress conditions.

Proceeding to optional step 510, the process 501 can include determining if the predicted human stress condition is anomalous compared to a normal range of human stress conditions in the region. For example, step 510 can include determining if the physiological information is one or more standard deviations from an average value of the physiological information. Alternatively, step 510 can include determining if the physiological information is two or more standard deviations, or three or more standard deviations from an average value of the physiological information.

Optionally, step 510 can include determining a threat condition corresponding to the predicted human stress condition. For example, one or more instances of an anomalous predicted human stress condition correspond to a person in the region having an intent to perform an act of terrorism, an intent to commit a crime, or telling a lie. For example, a person exhibiting parameters corresponding to nervousness may correspond to a person who may have such ill intent. Alternatively, one or more instances of an anomalous predicted human stress condition correspond to a person in the region having a health-related human stress condition. For example, heart or respiration anomalies, an abrupt loss of velocity, falling down, etc., may indicate physical distress that can be detected according to the process 501.

Optionally, the process 501 can include determining if the predicted human stress condition is anomalous in step 512. Optionally, if the predicted human stress condition is not anomalous, the process 501 can loop back to step 502, where the process can be repeated. Optionally, step 512 can include determining, as a function of the predicted human stress condition anomaly, whether to output the indication. If it is determined that an indication should be output, the process 501 can proceed to optional step 514 or can proceed directly to step 516.

In optional step 514, for a system that is equipped or operatively coupled to one or more cameras, an image such as a video image of a person can be captured. For example, the camera can be aligned to capturing a still or video image of the person 112 scanned by the micro-impulse radar with a camera 101. Proceeding to step 516, the still or video image of the person scanned by the micro-impulse radar can be displayed via a notification interface. This can include outputting the image of the person and a corresponding indicator of the predicted human stress condition to a computer display.

In step 516, an indication or notification of the predicted stress condition of the person is provided. The indication can be output via a notification interface. The notification interface can be configured to notify a person having a view of the region, or to a person (e.g. monitoring authority) that does not have a direct view of the region. The notification can provide information about the predicted stress condition to a guard, a police officer, a civil servant, a military officer or enlisted person, or a healthcare professional. For example, providing notification can include outputting information to a computer display. Optionally, providing notification can include providing the indication or notification to the person corresponding to the predicted stress condition.

Optionally, the method 501 can include a step of determining or inferring an identity of the person (not shown). For example, the identity of the person can be determined or inferred using biometric recognition (e.g., facial recognition, voice recognition, fingerprints, etc.) or by reading an identity indicia carried by the person. For example, an identity indicia can include an MIR transponder, a radio frequency tag, or other contact or non-contact identity card or tag.

When an identity is determined or inferred, providing an indication of the predicted stress condition of the person in step 516 can include providing the identity of the person. Optionally, correlating the physiological information to a predicted stress condition and determining if the predicted stress condition is anomalous in step 510 can be performed as a function of the identity of the person. For example, a given person may be naturally more nervous than another person. By determining the identity of a person, whether or not the predicted stress condition is anomalous can be informed by the normal range of attributes of the individual. For example, making this determination can be performed by reading a database including pre-determined stress parameters corresponding to the identity of the person.

Optionally, providing an indication of the predicted stress condition can include transmitting an alarm signal if the stress condition exceeds a limit. For example, the limit can correspond to a function of predicted stress conditions of a plurality of other persons previously scanned by the micro-impulse radar.

Optionally, at least some of the steps of the method 501 of FIG. 5 can be performed by one or more computers. The method steps as described above can thus be embodied as a non-transient computer-readable medium carrying computer instructions configured to cause a computer to perform the steps of the method 501.

Figure 6:
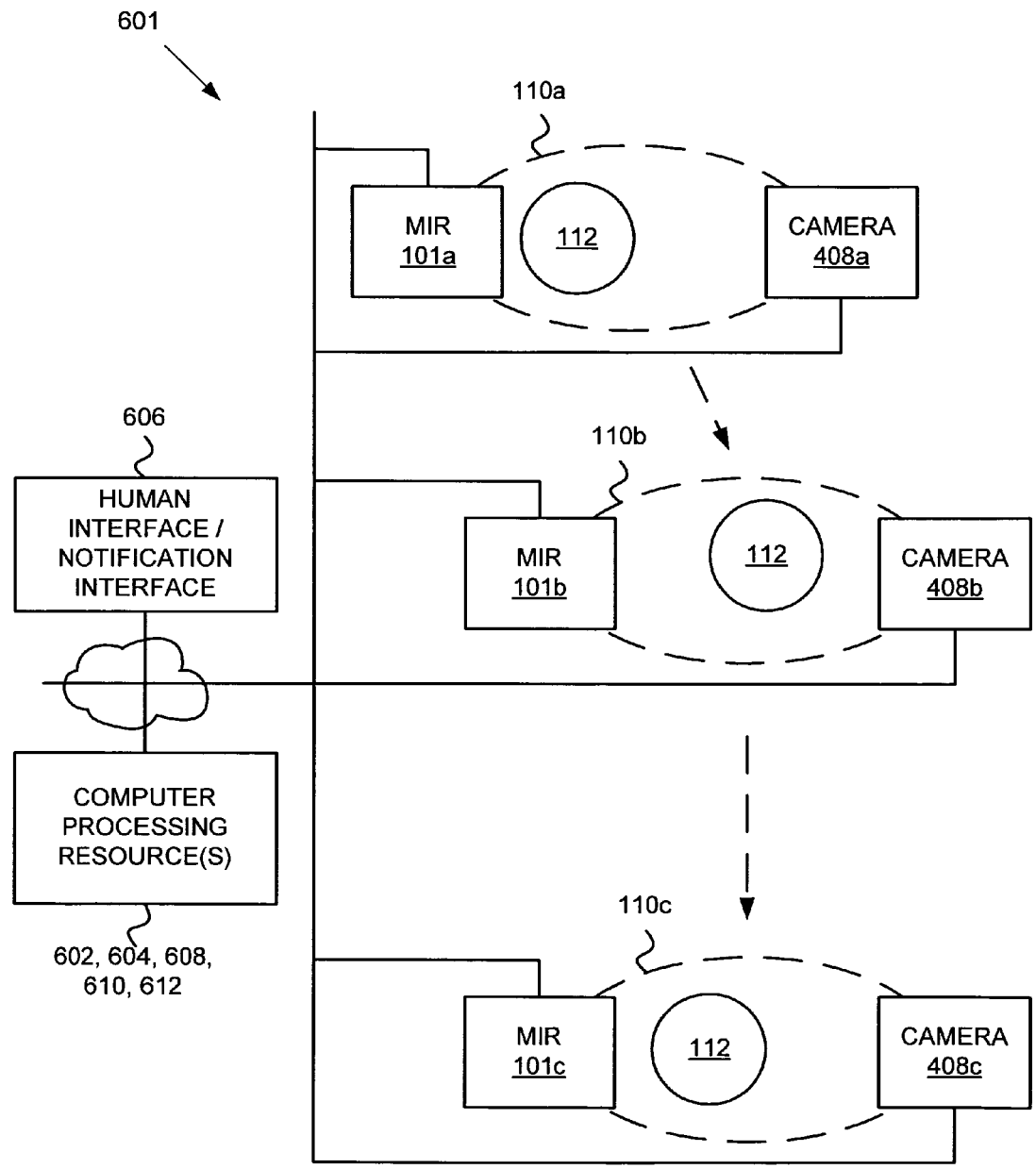
FIG. 6 is a block diagram of a system configured to track a person exhibiting a stress condition, according to an embodiment.

FIG. 6 is a block diagram of a system 601 configured to track a person 112 exhibiting a stress condition, according to an embodiment. A first MIR 101a can be configured to probe a first region 110a at least partially occupied by a person 112 and produce first MIR data related to one or more first attributes of the person 112. A first computer processing resource 602 can be operatively coupled to the first MIR 101a and configured to predict a stress condition of the person from the one or more first attributes of the person 112 included in the first MIR data. A camera 408a can be configured to capture one or more images of the person 112. The camera 408a can have a field of view including at least a portion of the first region 110a. A second computer processing resource 604, operatively coupled to the first computer processing resource 602 and the camera 408a, can be configured to correlate the predicted stress condition with the one or more images of the person 112. Optionally, the first and second computer processing resources 602, 604 can be the same computer processing resource. Optionally, the camera 408a can be remotely controllable, and the second computer processing resource 604 can be further configured to control the camera 408a to track the person 112.

Optionally, the system 601 can include at least one second camera 408b, 408c operatively coupled to the second computer processing resource 604 and configured to capture at least one image of the person 112 in at least a second region 110b, 110c. The second computing resource 604 can be configured to operate the at least one second camera 408b to track the person 112 as the person moves between a field-of-view 110a of the first camera 408a and the second region 408b.

The system 601 can further include a human interface 606 configured to provide information to a second person. A third computer processing resource 608 can be operatively coupled to the human interface 606, the second computer processing resource 604, the camera 408a, the at least one second camera 408b, 408c, and the first computer processing resource 602. The third computer processing resource 608 can be configured to present information including images of the person 112 and information related to the predicted stress condition of the person as the person 112 moves between regions 110a, 110b, 110c. Optionally, the third computer processing resource 608 and the second computer processing resource 604 can be the same computer processing resource.

At least one second MIR 101b, 101c can be operatively coupled to the first computing resource 602 and configured to probe at least the second region 110b, 110c and produce second MIR data related to one or more second attributes of the person 112. For example, the second attributes can be the same attributes as the first attributes at a second time corresponding to presence of the person 112 in the at least one second region 110b, 110c. Optionally, the second attributes can be different attributes than the first attributes of the person 112.

The system 601 can include a fourth computer processing resource 610 configured determine a risk condition corresponding to the person 112 from the images of the person and the first and at least second MIR data. Optionally, the fourth computer processing resource 610 can be the same as at least one of the first and second and third computer processing resources 602, 604, 608. The fourth computer processing resource 610 can be further configured to determine if the risk condition meets one or more criteria for notifying a second person. The system 601 can include a notification interface 606, and the fourth computer processing resource 610 can be configured to output data via the notification interface 606 corresponding to the risk condition.

A human interface 606 can be configured to provide information to a second person. A fifth computer processing resource 612 can be operatively coupled to the human interface 606, the second computer processing resource 604, the camera 408a, and the first computer processing resource 602. The fifth computer processing resource 612 can be configured to present information including the at least one image of the person 112 and information related to the predicted stress condition of the person 112. The fifth computer processing resource 612 and at least one of the first 602, second 604, third 608, and/or fourth 610 computer processing resource can be the same computer processing resource. The camera(s) 408a, 408b, 408c can be a video camera(s) configured to capture visible behaviors of the person 112.

In some embodiments, the human interface 606 can be replaced by or may be alternatively referred to as a "notification interface" 606. The term notification interface may be useful for applications where data output may or may not be output to an actual human. Thus, a notification interface 606 can include or substantially consist of a human interface, and can include a broader range of data or signal output structures or modules. The system 601 can include a notification interface 606 operatively coupled to the first computer processing resource 602 (and/or other computer processing resources). The first computer processing resource 602 can be configured to output notification data or a notification signal via the notification interface 606 for at least some predicted stress conditions. The first computer processing resource 602 can be configured to compare the predicted stress condition to a range of stress conditions, infer a risk condition, and output the notification data or notification signal when the risk condition corresponds to a condition where a risk is posed to the person or to others.

For example, the risk condition can correspond to a risk to the person, and the notification interface can be configured to alert a resource for offering aid to the person. Alternatively, the risk condition can correspond to a risk to others, and the notification interface can be configured to alert a resource for protecting others.

As indicated above, the MIR 101a and optional additional MIRs 101b, 101c can be configured to probe regions 110a, 101b, 101c at least partially occupied by a person 112 and produce first MIR data related to one or more first attributes of the person 112. The one or more first attributes of the person include one or more physical attributes, one or more physiological attributes, or one or more physical attributes and one or more physiological attributes. One or more physical attributes can include one or more of body size, body mass, height, body shape, posture, body permittivity, carried or otherwise associated articles, detectable body ornamentation, or body movements. One or more physiological attributes can include one or more of heart rate, respiration rate, heart anomaly, respiration anomaly, magnitude of heartbeat, magnitude of respiration, a rate or magnitude of inhalation, a rate or magnitude of exhalation, a tremor of all or part of a body, intracyclic characteristic of a heartbeat, intracyclic characteristic of respiration, or digestive muscle activity.

According to an embodiment, the system can look primarily at attributes including heart rate, respiration rate, and body movements (e.g., tremor or "jerkiness"). For example, these (and/or other) attributes can be indicative of a predicted stress condition that corresponds to high anxiety. Under this scenario, relatively high anxiety can be useful to predict in a person because a would-be criminal or terrorist may be expected to have unusual feelings of anxiety in his/her anticipation of committing a criminal or terrorist act. Such anxious feelings and corresponding physical or physiological "tells" may be made more evident under questioning. Thus the system 601 (and/or system 401 of FIG. 4 and/or system 801 of FIG. 8) can be used to augment an interview station, interrogation room, or other facility where anxiety may be disproportionally heightened in an "at risk" person.

The one or more MIRs 101a, 101b, 101c can also probe a response corresponding to one or more first attributes including a carried article such as a weapon (which may include a bomb, a chemical deterrent (e.g., "Mace"), or other objects that could be used during commission of a terrorist act or crime).

According to another embodiment, the system can look for a predicted stress condition that corresponds to physical distress. For example, this can be used to indicate and/or warn individuals in a marathon or triathlon that may be close to collapse, or otherwise spot persons who may be in need of assistance. In one embodiment, the system may be used to augment or provide a form of triage.

Figure 7:
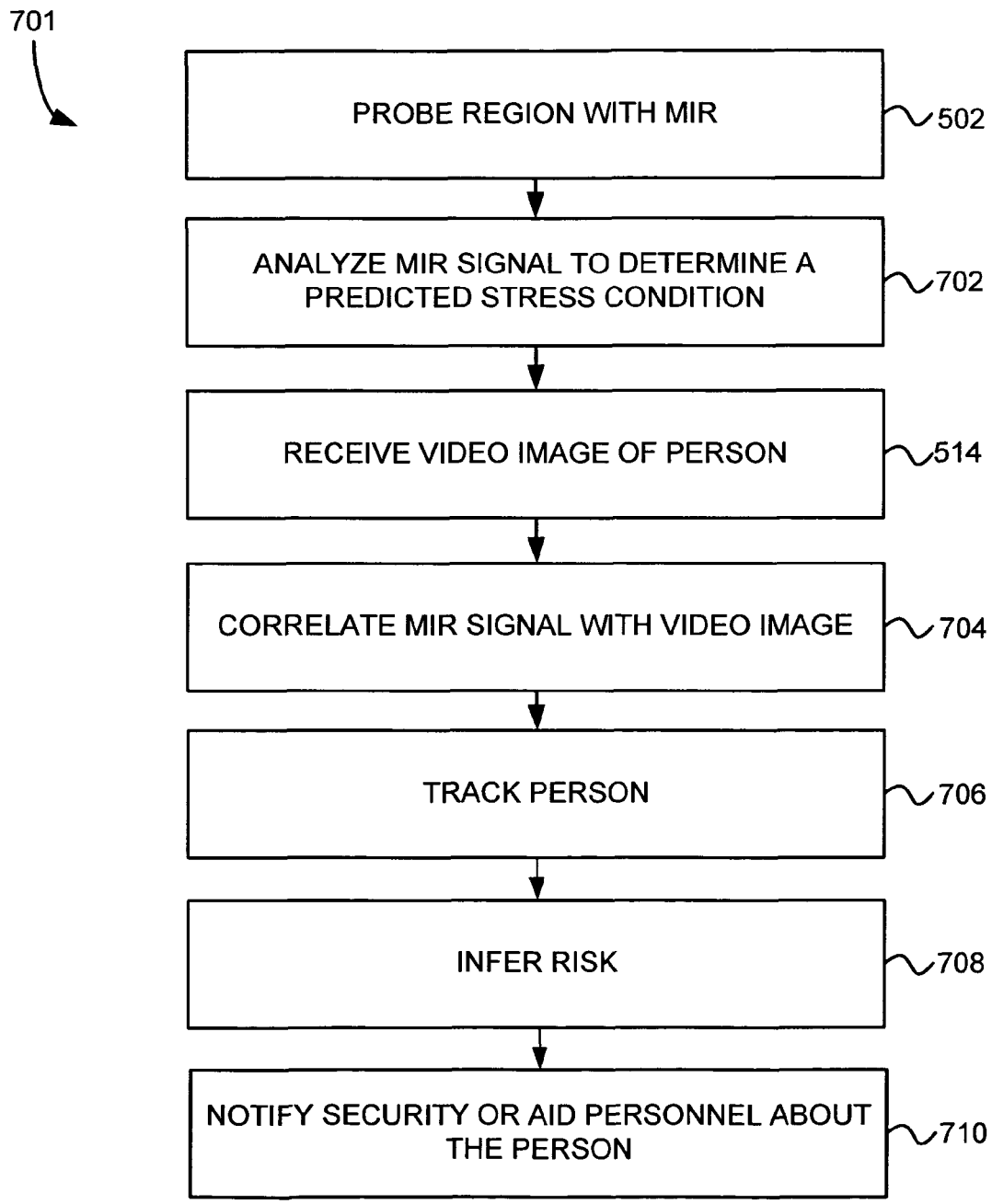
FIG. 7 is a flow chart illustrating a method for tracking a person with a stress condition, according to an embodiment.

FIG. 7 is a flowchart illustrating a method 701 for tracking a person with a stress condition, according to an embodiment. According to embodiments, the method of FIG. 7 can be performed using all or portions of the system 601 shown in FIG. 6 and/or other combinations of elements. Beginning at step 502, a person in a probing region is probed with a MIR to produce a MIR signal. Proceeding to step 702, the MIR signal is analyzed to determine a predicted stress condition corresponding to the person. The MIR signal can include data corresponding to one or more first attributes of the person. The one or more first attributes of the person can include one or more physical attributes, one or more physiological attributes, or one or more physical attributes and one or more physiological attributes. For example, one or more physical attributes can include one or more of body size, body mass, height, body shape, posture, body permittivity, carried or otherwise associated articles, detectable body ornamentation, or body movements. One or more physiological attributes can include one or more of heart rate, respiration rate, heart anomaly, respiration anomaly, magnitude of heartbeat, magnitude of respiration, a rate or magnitude of inhalation, a rate or magnitude of exhalation, a tremor of all or part of a body, intracyclic characteristic of a heartbeat, intracyclic characteristic of respiration, or digestive muscle activity. In one embodiment, the one or more first attributes include heart rate, respiration rate, and body movements. Optionally, the one or more attributes can include a carried article including a weapon.

Analyzing the MIR signal to determine a predicted stress condition corresponding to the person can include correlating the one or more first attributes to the predicted stress condition. For example, analyzing the MIR signal to determine a predicted stress condition can include comparing one or more first attributes of the person to one or more attributes corresponding to a range of stress conditions. The range of stress conditions can include a function of previously predicted stress conditions.

Proceeding to step 514, a video image of the person is received. Next, in step 704, the MIR signal is correlated with a video image of the person. For example, correlating the MIR signal with a video image of the person can include correlating a location of the person in the MIR signal to a location of the person in the video image. Step 704 can also include correlating a second MIR signal with a second video image of the person.

Proceeding to step 706, video image processing is used to track the movements of the person with at least one video camera. This can include determining a correlation between the video image and the second video image of the person. Step 706 can include tracking movements of the person as the person moves between fields of view of two or more video cameras, and/or controlling the at least one video camera to keep the person in a field-of-view of the at least one video camera.

Proceeding to optional step 708, a risk condition corresponding to the person can be inferred, for example, by comparing the predicted stress condition to a range of stress conditions. Optionally, step 708 can include correlating visible behavior of the person from the video image with the predicted stress condition of the person to infer a risk. For example, a would-be shoplifter may exhibit an increased heart rate and shallower breathing when the person passes a targeted article on the shelf. By comparing the video image to the predicted stress condition from the MIR signal, a location of risk can be inferred and extra security attention can be paid to the location of the risk. Alternatively, the visible behavior of the person may be location independent, but video information such as the person averting his/her gaze when answering a question can be combined with physiological and/or other physical data from the MIR signal to improve accuracy of lie detection/prediction/inference.

Proceeding to step 710, security and/or aid personnel can be notified, optionally only if the inferred risk is high enough to warrant notification.

The risk condition inferred in step 708 can correspond to a condition where a risk is posed to the person or to others. For example, if the MIR signal is analyzed to predict a stress condition corresponding to high anxiety, such condition may correspond to a risk for the person committing a crime, lying, or committing an act of terrorism. In such case, step 710 can include notifying a security authority about the person. Optionally, step 710 can include outputting media to the person, warning him/her of the consequences of a likely crime, thus providing a deterrent to committing a possible act. In another example, if the MIR signal is analyzed to predict a stress condition corresponding to physical distress, step 710 can include notifying assistance or aid personnel about the person. Optionally, step 710 can include outputting media to the person, which can, for example, alert the person to his/her physical distress, thus providing an impetus to seek medical attention or modify his/her exertion level.

Accordingly, step 710 can include alerting a resource for offering aid to the person, alerting a resource for protecting others, or alerting the person of the predicted stress condition. Step 710 can include outputting the video image of the person and the predicted stress condition of the person via a human interface, and/or outputting a plurality of video images of the person and a plurality of predicted stress conditions of the person via the human interface as the person moves.

Optionally, the method 701 can include selecting the person for output via the human interface as a function of the predicted stress condition of the person (not explicitly shown).

Optionally, at least some of the steps of the method 701 of FIG. 7 can be performed by one or more computers. The method steps as described above can thus be embodied as a non-transient computer-readable medium carrying computer instructions configured to cause a computer to perform the steps shown and described above.

Figure 8:
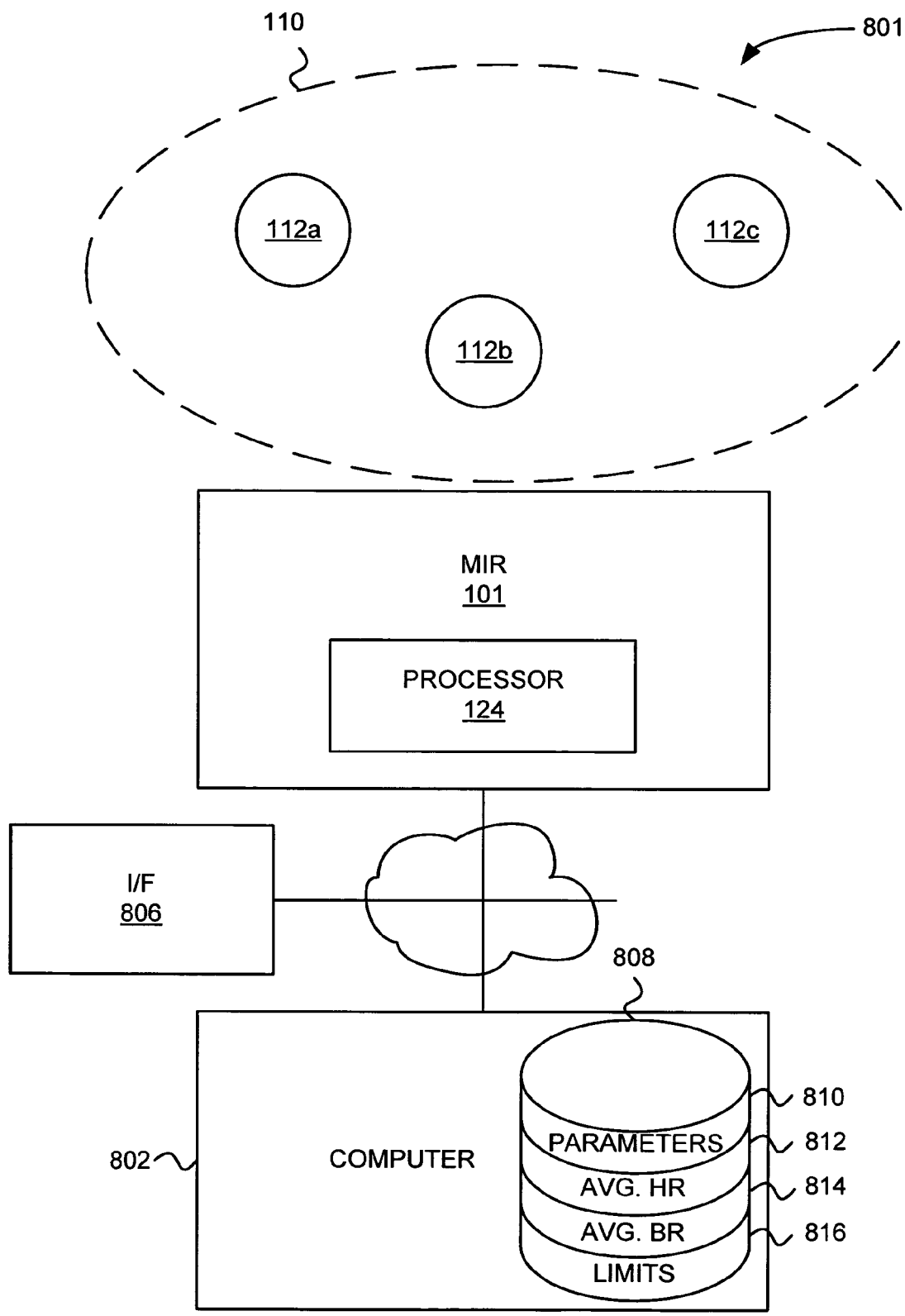
FIG. 8 is a block diagram of a system for evaluating a risk condition corresponding to a person, according to an embodiment.

FIG. 8 is a block diagram of a system 801 for evaluating a risk condition corresponding to a person 112*a*, according to an embodiment. A MIR 101 can be configured to probe a plurality of persons 112*a*, 112*b*, 112*c* to produce a micro-impulse radar signal. A processor 124 operatively coupled to the MIR can be configured to determine one or more physiological parameters from each of the plurality of persons 112*a*, 112*b*, 112*c*. A computer 804 operatively coupled to the processor 124 can be configured to receive the one or more physiological parameters, analyze the one or more physiological parameters, and indicate a person 112*a* whose one or more physiological parameters are functionally related to the one or more physiological parameters of other persons 112*b*, 112*c*.

As shown, the processor 124 can be integrated with the MIR 101. Alternatively or additionally, the processor 124 can be integrated with the computer or the processor can be separate from the MIR and the computer.

An interface 806 can be operatively coupled to the computer, and configured for indicating the person 112*a* whose one or more physiological parameters are functionally related to the one or more physiological parameters of other persons 112*b*, 112*c*. The interface 806 can include one or more of a remote device, a computer monitor, an alarm, a personal electronic device, a smart phone, and a pager.

According to an embodiment, indicating a person 112*a* whose one or more physiological parameters are functionally related to the one or more physiological parameters of other persons 112*b*, 112*c* can include transmitting an alarm signal if a function of the one or more physiological parameters exceeds a limit that is a function of the one or more physiological parameters of the other persons 112*b*, 112*c*. For example, indicating a person 112*a* whose one or more physiological parameters are functionally related to the one or more physiological parameters of other persons 112*b*, 112*c* can include indicating a person 112*a* whose one or more physiological parameters have a statistically significant difference from the one or more physiological parameters of the other persons 112*b*, 112*c*.

A non-transient computer-readable medium 808 can be operatively coupled to the computer 804. As shown, the non-transient computer-readable medium 808 can be integrated into the computer 804, for example, as a hard drive. The non-transient computer readable medium 808 can include data 810 corresponding to the one or more physiological parameters from the plurality of persons 112*b*, 112*c*. The computer 804 can be configured to compare the one or more physiological parameters corresponding to each person 112*a* to a function of the one or more physiological parameters 810 from the plurality of persons 112*b*, 112*c*. The non-transient computer-readable medium 808 can carry data corresponding to one or more averages of the physiological parameters from the plurality of persons 112*b*, 112*c*. For example, as shown, the non-transient computer-readable medium 808 can carry an average or weighted average of heart rates 812 and an average or weighted average of breathing or respiration rates 814. Optionally, the computer 804 can calculate the averages on-the-fly or can omit the averages and instead use one or more other functional relationships of parameters of other persons 112*b*, 112*c*. For example, the non-transient computer-readable medium 808 can carry data corresponding to one or more numbers of standard deviations from one or more averages of the physiological parameters from the plurality of persons 112*b*, 112*c*. The standard deviation and/or another function of the parameters from the plurality of persons 112b, 112c can optionally be expressed as one or more limits 816 against which the one or more physiological (and optionally, physical) parameters corresponding to each person 112a is compared. Before or after the comparison, the one or more physiological (and optionally, physical) parameters for a person of interest 112a can be combined or otherwise added to one or more functions 810, 812, 814, 816 of physiological parameters carried by the non-transient computer readable medium 808.

Optionally, the computer 804 can be configured to perform a joint fit between one or more physiological parameters from a plurality of persons 112a, 112b, 112c to determine one or more persons 112a exhibiting outlying physiological parameters.

The non-transient computer-readable medium 808 can carry data corresponding to a database, for example. The computer 804 can be configured to output a query statement including data corresponding to the one or more physiological parameters of a person 112a, and receive an indication of a risk condition corresponding the person 112a. The risk condition can be determined according to the functional relationship between the one or more physiological parameters of the person 112a and the one or more physiological parameters of the other persons 112b, 112c.

Optionally, the computer 804 can be further configured to determine whether to output the indication of the person 112a as a function of the risk condition.

By using one or more functions of physiological, and optionally physical, parameters that were previously received, the system 801 can adapt to changes in population stress level. Thus, the functional relationship can be selected to account temporal variations in the one or more physiological parameters of the other persons 112b, 112c. The functional relationship can also be selected to provide a variable sensitivity for the indication. For example, the functional relationship can be selected according to one or more of a threat level, a level of consequence related a false positive indication, or a level of consequence related to a false negative indication.

The one or more physiological parameters can include one or more of heart rate, respiration rate, heart anomaly, respiration anomaly, magnitude of heartbeat, magnitude of respiration, a rate or magnitude of inhalation, a rate or magnitude of exhalation, a tremor of all or part of a body, intracyclic characteristic of a heartbeat, intracyclic characteristic of respiration, or digestive muscle activity, for example. In one embodiment, the one or more physiological parameters includes one or more of heart rate, respiration rate, and body movements.

Moreover, as indicated above, the processor 124 can be further configured to determine one or more physical parameters from each of the plurality of persons 112a, 112b, 112c, and the computer can further configured to analyze the one or more physical parameters. Like the physiological parameter relationship, indicating a person 112a can include indicating a person 112a whose one or more physical parameters are functionally related to the one or more physical parameters of other persons 112b, 112c. The one or more physical parameters can include one or more of body size, body mass, height, body shape, posture, body permittivity, carried or otherwise associated articles, detectable body ornamentation, or body movements, for example. Optionally, the one or more physical parameters can include a carried article such as a weapon.

Figure 9:
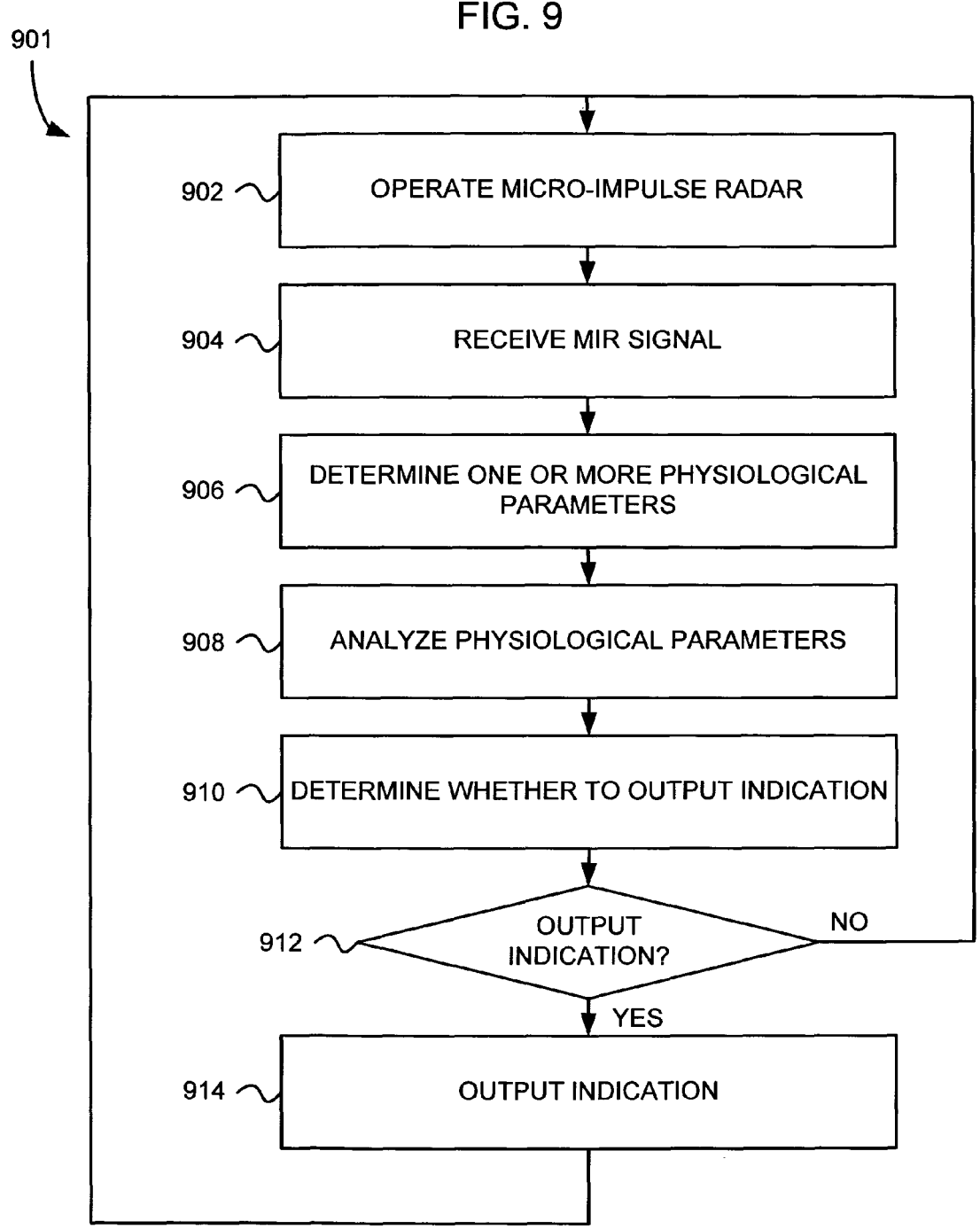
FIG. 9 is a flow chart illustrating method for evaluating a risk condition corresponding to a person, according to an embodiment.

FIG. 9 is a flowchart illustrating method 901 for evaluating a risk condition corresponding to a person, according to an embodiment. Starting in step 902, a MIR configured to probe a plurality of persons is operated to produce a MIR signal. Optionally, if a MIR is external to the system, the method 901 can start at step 904, where a MIR signal is received, or step 904 can represent a transmission of the MIR signal across an exposed interface. Proceeding to step 906, one or more physiological parameters from the MIR signal can be determined, such that each of the plurality of persons has a corresponding set of one or more physiological parameters. For example, the determination of the one or more physiological parameters can performed by the MIR, by a computer operatively coupled to the MIR, or the determination of the one or more physiological parameters can be performed by a computer separate from the MIR and separate from a computer that indicates the person.

As described above, the one or more physiological parameters can include one or more of heart rate, respiration rate, heart anomaly, respiration anomaly, magnitude of heartbeat, magnitude of respiration, a rate or magnitude of inhalation, a rate or magnitude of exhalation, a tremor of all or part of a body, intracyclic characteristic of a heartbeat, intracyclic characteristic of respiration, or digestive muscle activity, for example. According to an embodiment, the one or more physiological parameters includes one or more of heart rate, respiration rate, and body movements.

Proceeding to step 908, the one or more physiological parameters can be analyzed. Physiological parameter analysis can include comparing the one or more physiological parameters corresponding to each person to a function of the one or more physiological parameters from the plurality of persons. For example, comparing the one or more physiological parameters corresponding to each person to a function of the one or more physiological parameters from the plurality of persons can be performed using one or more database queries. Accordingly, analyzing the one or more physiological parameters can include outputting a query statement including data corresponding to the one or more physiological parameters of a person and receiving an indication of a risk condition corresponding the person. The risk condition can be determined according to the functional relationship between the one or more physiological parameters of the person and the one or more physiological parameters of the other persons.

The function of the one or more physiological parameters from the plurality of persons can correspond to one or more averages of the physiological parameters from the plurality of persons. Alternatively or additionally, the function of the one or more physiological parameters from the plurality of persons can correspond to one or more numbers of standard deviations from one or more averages of the physiological parameters from the plurality of persons and/or one or more limits against which the one or more physiological parameters corresponding to each person is compared. In an embodiment, analyzing the one or more physiological parameters can include performing a joint fit between one or more physiological parameters from a plurality of persons to determine one or more persons exhibiting outlying physiological parameters.

Proceeding to optional steps 910 and 912, the process can include deciding whether to output an indication of the person's physiological parameters or risk condition, or to suppress reporting. For example, the process 901 can choose to transmit an alarm signal or otherwise report the indication if a function of the one or more physiological parameters exceeds a limit that is a function of the one or more physiological parameters of the other persons. This can include choosing to output an indication of a person whose one or more physiological parameters have a statistically significant difference from the one or more physiological parameters of the other persons. In other words, determining whether to output the indication of the person can be performed as a function of a risk condition corresponding to the person.

The functional relationship between the parameters corresponding to an individual and parameters corresponding to other persons can be selected to provide a variable sensitivity for the indication. This can be used to account temporal variations in the one or more physiological parameters of the other persons and/or according to one or more of a threat level, a level of consequence related a false positive indication, or a level of consequence related to a false negative indication. If a person's physiological (and optionally, physical) parameters have a functional relationship to a function of other persons' parameters that indicate a risk condition exists, the process 901 can proceed to step 914. If a person's physiological (and optionally, physical) parameters have a functional relationship to a function of other persons' parameters that indicate a risk condition exists, the process 901 can loop back to step 902 (or 904) and an analysis of the next person can be performed.

Step 914 includes indicating a person whose one or more physiological parameters are functionally related to the one or more physiological parameters of other persons. That is, if the physiological parameters for the person meet a predetermined functional relationship or do not meet a different predetermined functional relationship, or if a joint fit indicates an indication should be output, the step 914 can be executed. Indication can be provided through one or more of a remote device, a computer monitor, an alarm, a personal electronic device, a smart phone, and a pager.

Optionally, the process 901 can include determining one or more physical parameters from each of the plurality of persons (in step 906) and, in step 908, analyzing the one or more physical parameters. The physical parameters can be analyzed in relation to the parameters of other persons in manners similar to approaches described above. For example, one or more physical parameters can include one or more of body size, body mass, height, body shape, posture, body permittivity, carried or otherwise associated articles, detectable body ornamentation, or body movements. According to an embodiment, the one or more physical parameters can include a carried article such as a weapon.

Optionally, at least some of the steps of the method 901 of FIG. 9 can be performed by one or more computers. The method steps as described above can thus be embodied as a non-transient computer-readable medium carrying computer instructions configured to cause a computer to perform the steps shown and described above.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., " a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A surveillance system, comprising:
   a micro-impulse radar configured to survey a region; and
   a controller configured to,
      receive an input signal from the micro-impulse radar,
      extract from the signal one or more physical or physiological attributes of more
   than one person corresponding to a human stress condition,
      compare the extracted one or more physical physiological attributes of the more than one person corresponding to the human stress condition to calculate a statistical average value of the one or more physical or physiological attributes corresponding to the human stress condition,
determine if the extracted one or more physical or physiological attributes corresponding to the human stress condition indicate a predicted human stress condition for at least a single person in the region at least partially based on the statistical average value by determining if the extracted one or more physical or physiological attributes corresponding to the human stress condition for the at least a single person in the region fall outside of a predetermined deviation from the statistical average value, and
base at least in part on the determination of whether or not the one or more physical or physiological attributes corresponding to the human stress condition for the at least a single person fall outside of the predetermined deviation, output a notification signal.

2. The surveillance system of claim 1, wherein the one or more physical or physiological attributes includes one or more physical and one or more physiological attributes.

3. The surveillance system of claim 1, wherein the controller is further configured to receive or determine a range of the one or more physical or physiological attributes corresponding to normal range of human stress conditions in the region.

4. The surveillance system of claim 1, wherein the controller is further configured to determine if the predicted human stress condition is anomalous compared to a normal range of human stress conditions in the region.

5. The surveillance system of claim 1, further comprising a notification interface operatively coupled to the controller; and
wherein the notification signal is output via the notification interface.

6. The surveillance system of claim 5, wherein the notification interface includes an apparatus configured to project an optical designation onto or near a person exhibiting an anomalous predicted stress condition.

7. The surveillance system of claim 1, further comprising:
a camera operatively coupled to the controller and configured to capture a still or video image of a person probed by the micro-impulse radar.

8. The surveillance system of claim 7, wherein the controller is further configured to display the still or video image of the person probed by the micro-impulse radar via a notification interface.

9. The surveillance system of claim 1, wherein the controller is further configured to determine or infer an identity of a person in the region.

10. The surveillance system of claim 9, wherein a magnitude of the predicted stress condition is determined as a function of the identity of the person.

11. The surveillance system of claim 7, further comprising:
a computer display; and
wherein the controller is configured to output to the computer display an image of the person in the region and a corresponding indicator of the predicted human stress condition corresponding to the person in the region.

12. The surveillance system of claim 1, wherein the controller is further configured to determine a threat condition corresponding to the predicted human stress condition.

13. The surveillance system of claim 1, wherein the controller is configured to determine whether to output the notification signal as a function of time of day, a security threat status, or a security clearance status of a person in the region.

14. The surveillance system of claim 1, wherein the controller is further configured to predict the human stress condition.

* * * * *

UNITED STATES PATENT AND TRADEMARK OFFICE
CERTIFICATE OF CORRECTION

PATENT NO. : 8,884,813 B2  
APPLICATION NO. : 12/930254  
DATED : November 11, 2014  
INVENTOR(S) : Bangera et al.

Page 1 of 1

It is certified that error appears in the above-identified patent and that said Letters Patent is hereby corrected as shown below:

In the claims

Column 24, Lines 66-67, Claim 1 "compare the extracted one or more physical physiological attributes" should read --compare the extracted one or more physical or physiological attributes--

Column 25, Line 15, Claim 1 "base at least in part on the determination of whether or" should read --based at least in part on the determination of whether or--

Column 25, Lines 25-26, Claim 3 "corresponding to normal range of human stress conditions in the region." should read --corresponding to a normal range of human stress conditions in the region.--

Signed and Sealed this
Twenty-third Day of February, 2016

Michelle K. Lee
*Director of the United States Patent and Trademark Office*